US009322003B2

(12) United States Patent
Nguyen et al.

(10) Patent No.: US 9,322,003 B2
(45) Date of Patent: Apr. 26, 2016

(54) CLONING, EXPRESSION AND USE OF ACID PHOSPHOLIPASES

(71) Applicant: AB Enzymes GMBH, Darmstadt (DE)

(72) Inventors: Khanh Quoc Nguyen, Reichelsheim (DE); Kornelia Titze, Muehltal (DE); Tatiana Schwarz, Erzhausen (DE); Silvia Paladino, Happenheim (DE); Volker Marschner, Bickenbach (DE); Patrick Lorenz, Lorsch (DE)

(73) Assignee: AB ENZYMES GMBH, Darmstadt (DE)

( * ) Notice: Subject to any disclaimer, the term of this patent is extended or adjusted under 35 U.S.C. 154(b) by 0 days.

(21) Appl. No.: 14/692,230

(22) Filed: Apr. 21, 2015

(65) Prior Publication Data

US 2015/0299680 A1    Oct. 22, 2015

Related U.S. Application Data

(62) Division of application No. 13/502,945, filed as application No. PCT/EP2010/066234 on Oct. 27, 2010, now Pat. No. 9,045,713.

(30) Foreign Application Priority Data

Oct. 28, 2009  (DE) .................... 10 2009 051 013

(51) Int. Cl.
*C12N 9/18*      (2006.01)
*A23D 9/02*     (2006.01)
(Continued)

(52) U.S. Cl.
CPC .. *C12N 9/18* (2013.01); *A23D 9/00* (2013.01); *A23D 9/02* (2013.01); *A23J 7/00* (2013.01);
(Continued)

(58) Field of Classification Search
None
See application file for complete search history.

(56) References Cited

U.S. PATENT DOCUMENTS 5,264,367 A   11/1993  Aalrust et al.
5,538,874 A   7/1996  Hattori et al.

(Continued)

FOREIGN PATENT DOCUMENTS

EP      0513709 A2    11/1992
EP      0808903 A2    11/1997
(Continued)

OTHER PUBLICATIONS

Chica et al. Curr Opin Biotechnol. Aug. 2005;16(4):378-84.*
(Continued)

*Primary Examiner* — Christian Fronda
(74) *Attorney, Agent, or Firm* — Mintz Levin Cohn Ferris Glovsky and Popeo, P.C.; Peter F. Corless, Esq.; Daniel W. Clarke

(57) ABSTRACT

The invention relates to a DNA sequence, which codes for a polypeptide having phospholipase activity essentially without lipase activity, characterized in that the DNA sequence is selected from a) DNA sequences that comprise a nucleotide sequence according to SEQ ID NO: 1, b) DNA sequences that comprise the coding sequence according to SEQ ID NO: 1, c) DNA sequences that code for the protein sequence according to SEQ ID NO: 2, d) DNA sequences that are coded for by the plasmid pPL3940-Topo2.5 with the restriction map according to FIG. 7, which is deposited under accession number DSM 22741, e) DNA sequences that hybridize under stringent conditions with one of the DNA sequences according to a), b), c) or d), f) DNA sequences that are related to the DNA sequences according to a), b), c), d) or e) due to the degeneration of the genetic code, and g) complementary strands to the sequences according to a) to f), wherein the DNA sequence is preferably derived from *Aspergillus*, and more preferably from *Aspergillus fumigatus*, and a polypeptide having phospholipase activity essentially without lipase activity selected from a) a polypeptide which is coded for by the coding part of a DNA sequence as defined above, b) a polypeptide having the sequence according to SEQ ID NO: 2 or a sequence derived therefrom, which may be obtained by substitution, addition, deletion of one or more amino acid(s), c) a polypeptide having a sequence that has at least 83% identity with the amino acids 1 to 299 of SEQ ID NO: 2, d) a polypeptide which is coded for by a nucleic acid sequence which hybridizes under stringent conditions with (i) nucleotides 55 to 1106 of SEQ ID NO: 1, (ii) the cDNA sequence contained in nucleotides 55 to 1106 of SEQ ID NO: 1, (iii) a partial sequence of (i) or (ii) composed of at least 100 nucleotides, or (iv) a complementary strand of (i), (ii) or (iii), e) a variant of the polypeptide having SEQ ID NO: 2, comprising a substitution, deletion and/or insertion of one or more amino acid(s), f) allelic variants to amino acid sequences a) to e).

9 Claims, 9 Drawing Sheets

Figure 1:
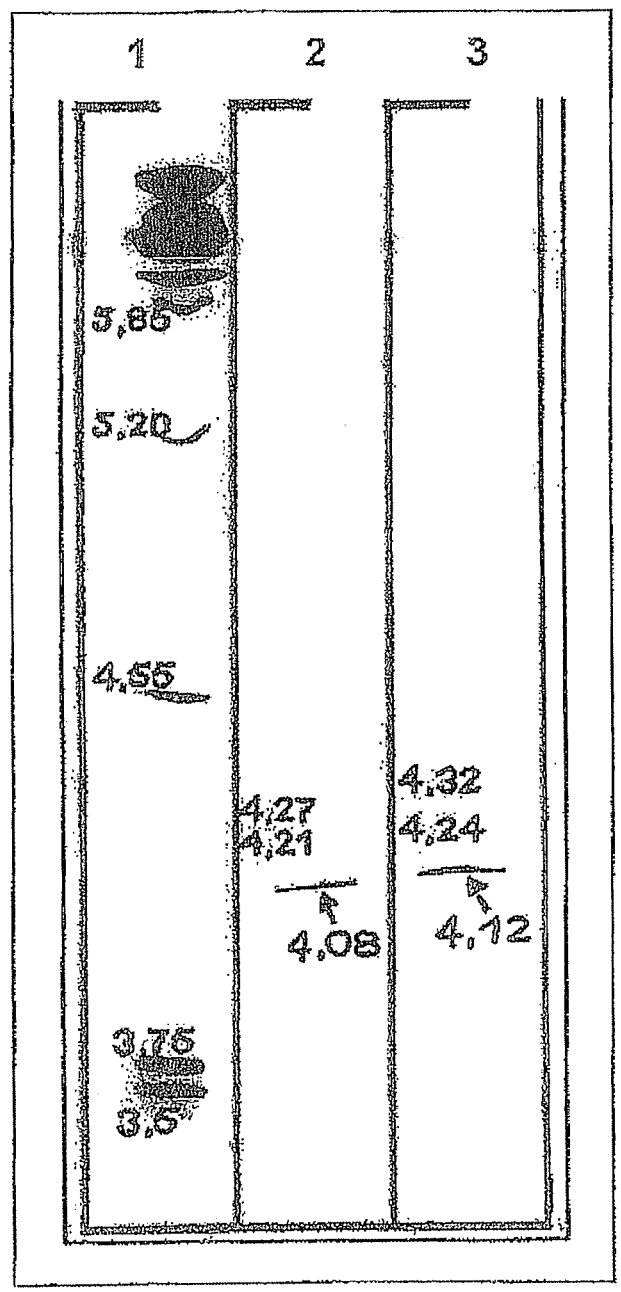

(51) Int. Cl.

| | | |
|---|---|---|
| *A23D 9/00* | (2006.01) | |
| *A23J 7/00* | (2006.01) | |
| *A23K 1/165* | (2006.01) | |
| *C11B 3/00* | (2006.01) | |
| *C12N 9/16* | (2006.01) | |

(52) U.S. Cl.
CPC .............. *A23K 1/1653* (2013.01); *C11B 3/00* (2013.01); *C11B 3/003* (2013.01); *C12N 9/16* (2013.01); *A23V 2002/00* (2013.01); *C12Y 301/01004* (2013.01); *C12Y 301/01005* (2013.01); *C12Y 301/01032* (2013.01)

(56) References Cited

U.S. PATENT DOCUMENTS

| 5,965,422 | A | 10/1999 | Loffler et al. |
|---|---|---|---|
| 6,140,094 | A | 10/2000 | Loffler et al. |
| 9,045,713 | B2 | 6/2015 | Nguyen et al. |
| 2007/0134777 | A1 | 6/2007 | Dayton et al. |
| 2011/0287141 | A1 | 11/2011 | Nguyen et al. |

FOREIGN PATENT DOCUMENTS

| EP | 0904357 | A1 | 3/1999 |
|---|---|---|---|
| EP | 1788080 | A1 | 5/2007 |
| WO | WO-9831790 | A1 | 7/1998 |
| WO | WO-9845453 | A1 | 10/1998 |
| WO | WO-03012071 | A2 | 2/2003 |
| WO | WO-03060112 | A1 | 7/2003 |
| WO | WO-03097825 | A2 | 11/2003 |
| WO | WO-2008040465 | A1 | 4/2008 |
| WO | WO-2008040466 | A1 | 4/2008 |
| WO | WO-2008094847 | A1 | 8/2008 |

OTHER PUBLICATIONS

Sen et al. Appl Biochem Biotechnol. Dec. 2007;143(3):212-23.*
Accession B0Y214. Apr. 8, 2008.*
Accession XP.sub.—748138. Feb. 19, 2008.
Database EMBL, DM383387; Feb. 10, 2010, "Novel phospholipases and uses thereof".
Fedorova et al., "Genomic Islands in the Pathogenic Filamentous Fungus Aspergillus fumigatus", PloS Genentics, 4(4), pp. 1-12 (2008).
Mustranta et al., "Comparison of Lipases and Phospholipases in the Hydrolysis of Phospholipids", Process Biochemistry, 30(5), pp. 393-401 (1995).
Nierman et al., "Genomic sequence of the pathogenic and allergenic filamentous fungus Aspergillus fumigatus", Nature, 438(7071), pp. 1151-1156 (2005).
Shen et al., "Characterisation and expression of pholospholipases B from the opportunistic fungus Aspergillus fumigatus", FEMS Microbiology Letters, 239(1), pp. 87-93 (2004).
Winter et al., "Application of phospholipases in the edible oil industry", Fett/Lipid, 100(4-5), pp. 152-156 (1998).

* cited by examiner

```
  1 AGAGTCTGCC TATATTCTCT CTGAAAGGGT TGTCTTGAGT ATAGCTTCGG
 51 CATCATGGTC CAGTTCAAGT CTGTCCGTAC GCTGGCTGTC GCGGCGTTTG
         m  v  q  f  k  s  v  r  t  l  a  v  a  a  f
101 CTGCGCTGGG TGCTGCGGCG CCAGCAGGGT TGGCTGAGCG AGGTATGTCC
     a  a  l  g  a  a  a  p  a  g  l  a  e  r
151 GACGCTTCCT TAAGATTGGC TCTGGGTGGT GCTAACTACT AAGTAGATGT
                                                       d
201 GTCCGCGTCG GTGCTGCAAA AGTTGTCGTT GTTTGCGCAA TACTCTGCTG
     v  s  a  s  v  l  q  k  l  s  l  f  a  q  y  s  a
251 CCGCTTATTG TACCAACAAC ATCAATTCCA CGGGCACCAA GCTGACGTGC
     a  a  y  c  t  n  n  i  n  s  t  g  t  k  l  t  c
301 TCTGCTGGAA ACTGTCCTCT GGTCGAGGCA GCCAACACCA AGACCCTTGC
     s  a  g  n  c  p  l  v  e  a  a  n  t  k  t  l
351 GGAGTTCTAC GAGTAGGTCG ATCCCATGCA TGAGTAGCTC GCATATCTAA
     a  e  f  y  e
401 CAGAGCTGGT AGTTCCGAAT CGTTTGGAGA CACGGCAGGC TTCTTGGTTG
           a  g  s  s  e  s  f  g  d  t  a  g  f  l  v
451 CAGACACCAC AAACAAGCTA CTCGTGGTCT CTTTCAGAGG AAGCCGCACG
     a  d  t  n  k  l  l  v  v  s  f  r  g  s  r  t
501 ATAGACAACT GGATTGCGAA TCTGGACTTT GTTCTGGACA GTGTCAGTGA
     i  d  n  w  i  a  n  l  d  f  v  l  d  s  v  s
551 TATTTGCAGC GGATGCGCCG CACACGGGGG CTTCTGGAAG TCCTGGGAAG
     d  i  c  s  g  c  a  a  h  g  g  f  w  k  s  w  e
601 TTGTTGCCAA TTCGCTGACG ACCGAGCTCA ACTCTGCGGT TAACACTTAC
     v  v  a  n  s  l  t  t  e  l  n  s  a  v  n  t  y
651 CCTGGCTATA CCATTGTCTT CACTGGACAT AGCCTCGGCG CTGCTCTTGC
     p  g  y  t  i  v  f  t  g  h  s  l  g  a  a  l
701 AACACTGGGG GCTACTACGC TGCGGAAAGC AGGGATTCCC ATTCAGCTGG
     a  t  l  g  a  t  t  l  r  k  a  g  i  p  i  q  l
751 TAAGTCATCC CTTGTCAACT TATGCAAGGG CGCAATGGCA CTAATTGATT

801 GTGAAGTATA ATTACGGATC CCCCCGTGTT GGAAACACGG CCTTGGCAAC
                  y  n  y  g  s  p  r  v  g  n  t  a  l
851 ATACATCACC GCACAGGGTC CCAATTACCG TGTCACACAC ACAAACGATA
     t  y  i  t  a  q  g  p  n  y  r  v  t  h  t  n  d
901 TTGTGCCCAG ACTCCCGCCC CAAGCTTTTG GCTTCAGCCA CCTTAGCCCG
     i  v  p  r  l  p  p  q  a  f  g  f  s  h  l  s  p
```

FIG. 4A

```
 951  GAGTACTGGA TCACGAGCGG CGACAACGTG CCTGTCACGA CGTCTGATAT
       e  y  w  i  t  s  g  d  n  v  p  v  t  t  s  d
1001  CACGGTCATC CAGGGAATCG ACTCAGACGC TGGAAATTCG GGAGAGGATA
       i  t  v  i  q  g  i  d  s  d  a  g  n  s  g  e  d
1051  TCACCAGCAT CGAGGCCCAT AATTGGTATC TCGGCGATAT TGATGCTTGT
       i  t  s  i  e  a  h  n  w  y  l  g  d  i  d  a  c
1101  CAATGAGACT ATAAGCGGAG TATATAACAG CTTTGGATAG TATAAAAGG
       q  -
1150  GCCAGTACAC TTGGGCTAAC GCATGAGGAA TGACATTGAT GACCTATCTT
1200  GCCAATGCAA TCAGTTTTAT AAGGAGAGTC CTCATGATTG ATTATGTCAA
1250  TTGGTATGGA GTAGAAATAA ACTGTACAGA TCTCTGGATC CGCCGAGTGG
1300  ACATTCATTA TGAGGTTCTG GGGAAGTTTG TTTGGTTTGG ACTTTGACAC
1350  CTGGAGTTTA TCCCCATCTC CATCAACTCG TCTGATTGTG GCTCGACGAG
1400  CGCATTCTTA CTGAATGCTC ATCTGTTTGA ATAGAATATG ATTAACGAGC
1450  AGTAACTCCC ATTCCTTTCG AACGCCTTTG CGCAATTGAA TCCATCCTTC
1500  CAACCCGTGC AACTTCAACC AGCCGCCCGG GCGACTCTGC GCATTCTCAA
1550  CATCTCTCGA CCCGCCGCGA TGGTCGCTGC TCCATGCTGC TGATACTCTT
1600  CTGTTATCAG TAATCACGGA AATTGTCATA
```

FIG.4B

```
   1  AGAGTCTGCC TATATTCTCT CTGAAAGGGT TGTCTTGAGT ATAGCTTCGG
  51  CATCATGGTC CAGTTCAAGT CTGTCCGTAC GCTGGCTGTC GCGGCGTTTG
 101  CTGCGCTGGG TGCTGCGGCG CCAGCAGGGT TGGCTGAGCG AGGTATGTCC
 151  GACGCTTCCT TAAGATTGGC TCTGGGTGGT GCTAACTACT AAGTAGATGT
 201  GTCCGCGTCG GTGCTGCAAA AGTTGTCGTT GTTTGCGCAA TACTCTGCTG
 251  CCGCTTATTG TACCAACAAC ATCAATTCCA CGGGCACCAA GCTGACGTGC
 301  TCTGCTGGAA ACTGTCCTCT GGTCGAGGCA GCCAACACCA AGACCCTTGC
 351  GGAGTTCTAC GAGTAGGTCG ATCCCATGCA TGAGTAGCTC GCATATCTAA
 401  CAGAGCTGGT AGTTCCGAAT CGTTTGGAGA CACGGCAGGC TTCTTGGTTG
 451  CAGACACCAC AAACAAGCTA CTCGTGGTCT CTTTCAGAGG AAGCCGCACG
 501  ATAGACAACT GGATTGCGAA TCTGGACTTT GTTCTGGACA GTGTCAGTGA
 551  TATTTGCAGC GGATGCGCCG CACACGGGGG CTTCTGGAAG TCCTGGGAAG
 601  TTGTTGCCAA TTCGCTGACG ACCGAGCTCA ACTCTGCGGT TAACACTTAC
 651  CCTGGCTATA CCATTGTCTT CACTGGACAT AGCCTCGGCG CTGCTCTTGC
 701  AACACTGGGG GCTACTACGC TGCGGAAAGC AGGGATTCCC ATTCAGCTGG
 751  TAAGTCATCC CTTGTCAACT TATGCAAGGG CGCAATGGGA CTAATTGATT
 801  GTGAAGTATA ATTACGGATC CCCCGTGTT GGAAACACGG CCTTGGCAAC
 851  ATACATCACC GCACAGGGTC CCAATTACCG TGTCACACAC ACAAACGATA
 901  TTGTGCCCAG ACTCCCGCCC CAAGCTTTTG GCTTCAGCCA CCTTAGCCCG
 951  GAGTACTGGA TCACGAGCGG CGACAACGTG CCTGTCACGA CGTCTGATAT
1001  CACGGTCATC CAGGGAATCG ACTCAGACGC TGGAAATTCG GGAGAGGATA
1051  TCACCAGCAT CGAGGCCCAT AATTGGTATC TCGGCGATAT TGATGCTTGT
1101  CAATGAGACT ATAAGCGGAG TATATAACAG CTTTGGATAG TATAAAAGG
1150  GCCAGTACAC TTGGGCTAAC GCATGAGGAA TGACATTGAT GACCTATCTT
1200  GCCAATGCAA TCAGTTTTAT AAGGAGAGTC CTCATGATTG ATTATGTCAA
1250  TTGGTATGGA GTAGAAATAA ACTGTACAGA TCTCTGGATC CGCCGAGTGG
1300  ACATTCATTA TGAGGTTCTG GGGAAGTTTG TTTGGTTTGG ACTTTGACAC
1350  CTGGAGTTTA TCCCCATCTC CATCAACTCG TCTGATTGTG GCTCGACGAG
1400  CGCATTCTTA CTGAATGCTC ATCTGTTTGA ATAGAATATG ATTAACGAGC
1450  AGTAACTCCC ATTCCTTTCG AACGCCTTTG CGCAATTGAA TCCATCCTTC
1500  CAACCCGTGC AACTTCAACC AGCCGCCCGG GCGACTCTGC GCATTCTCAA
1550  CATCTCTCGA CCCGCCGCGA TGGTCGCTGC TCCATGCTGC TGATACTCTT
1600  CTGTTATCAG TAATCACGGA AATTGTCATA
```

Figure 5

```
  1  MVQFKSVRTL AVAAFAALGA AAPAGLAERD VSASVLQKLS LFAQYSAAAY
 51  CTNNINSTGT KLTCSAGNCP LVEAANTKTL AEFYEAGSSE SFGDTAGFLV
101  ADTTNKLLVV SFRGSRTIDN WIANLDFVLD SVSDICSGCA AHGGFWKSWE
151  VVANSLTTEL NSAVNTYPGY TIVFTGHSLG AALATLGATT LRKAGIPIQL
201  YNYGSPRVGN TALATYITAQ GPNYRVTHTN DIVPRLPPQA FGFSHLSPEY
251  WITSGDNVPV TTSDITVIQG IDSDAGNSGE DITSIEAHNW YLGDIDACQ
```

Figure 6

```
SEQUENCE LISTING

<160> NUMBER OF SEQ ID NOS: 5

<210> SEQ ID NO 1
<211> LENGTH: 1629
<212> TYPE: DNA
<213> ORGANISM: Aspergillus fumigatus
<220> FEATURE:
<221> NAME/KEY: CDS
<222> LOCATION: (55)..(142)
<220> FEATURE:
<221> NAME/KEY: CDS
<222> LOCATION: (197)..(362)
<220> FEATURE:
<221> NAME/KEY: CDS
<222> LOCATION: (404)..(749)
<220> FEATURE:
<221> NAME/KEY: CDS
<222> LOCATION: (807)..(1103)

<400> SEQUENCE: 1
agagtctgcc tatattctct ctgaaagggt tgtcttgagt atagcttcgg catc atg      57
                                                              Met
                                                              1 gtc cag ttc aag tct gtc cgt acg ctg gct gtc gcg gcg ttt gct gcg    105
Val Gln Phe Lys Ser Val Arg Thr Leu Ala Val Ala Ala Phe Ala Ala
        5                  10                  15 ctg ggt gct gcg gcg cca gca ggg ttg gct gag cga g gtatgtccga       152
Leu Gly Ala Ala Ala Pro Ala Gly Leu Ala Glu Arg
            20                  25 cgcttcctta agattggctc tgggtggtgc taactactaa gtag at gtg tcc gcg    207
                                                Asp Val Ser Ala
                                                30 tcg gtg ctg caa aag ttg tcg ttg ttt gcg caa tac tct gct gcc gct    255
Ser Val Leu Gln Lys Leu Ser Leu Phe Ala Gln Tyr Ser Ala Ala Ala
    35                  40                  45 tat tgt acc aac aac atc aat tcc acg ggc acc aag ctg acg tgc tct    303
Tyr Cys Thr Asn Asn Ile Asn Ser Thr Gly Thr Lys Leu Thr Cys Ser
50                  55                  60                  65 gct gga aac tgt cct ctg gtc gag gca gcc aac acc aag acc ctt gcg    351
Ala Gly Asn Cys Pro Leu Val Glu Ala Ala Asn Thr Lys Thr Leu Ala
```

|  |  |  |  |  |  |  |  |  |  |  |  |  |  |  | |
|---|---|---|---|---|---|---|---|---|---|---|---|---|---|---|---|
|  |  |  | 70 |  |  |  | 75 |  |  |  | 80 |  |  |  | |
| gag | ttc | tac | ga | gtaggtcgat | cccatgcatg | agtagctcgc | atatctaaca | g | a |  |  |  |  |  | 404 |
| Glu | Phe | Tyr | Glu |  |  |  |  |  |  |  |  |  |  |  | |
|  |  |  | 85 |  |  |  |  |  |  |  |  |  |  |  | |

```
gct ggt agt tcc gaa tcg ttt gga gac acg gca ggc ttc ttg gtt gca    452
Ala Gly Ser Ser Glu Ser Phe Gly Asp Thr Ala Gly Phe Leu Val Ala
             90                  95                 100 gac acc aca aac aag cta ctc gtg gtc tct ttc aga gga agc cgc acg    500
Asp Thr Thr Asn Lys Leu Leu Val Val Ser Phe Arg Gly Ser Arg Thr
            105                 110                 115 ata gac aac tgg att gcg aat ctg gac ttt gtt ctg gac agt gtc agt    548
Ile Asp Asn Trp Ile Ala Asn Leu Asp Phe Val Leu Asp Ser Val Ser
            120                 125                 130 gat att tgc agc gga tgc gcc gca cac ggg ggc ttc tgg aag tcc tgg    596
Asp Ile Cys Ser Gly Cys Ala Ala His Gly Gly Phe Trp Lys Ser Trp
135                 140                 145 gaa gtt gtt gcc aat tcg ctg acg acc gag ctc aac tct gcg gtt aac    644
Glu Val Val Ala Asn Ser Leu Thr Thr Glu Leu Asn Ser Ala Val Asn
150                 155                 160                 165 act tac cct ggc tat acc att gtc ttc act gga cat agc ctc ggc gct    692
Thr Tyr Pro Gly Tyr Thr Ile Val Phe Thr Gly His Ser Leu Gly Ala
                170                 175                 180 gct ctt gca aca ctg ggg gct act acg ctg cgg aaa gca ggg att ccc    740
Ala Leu Ala Thr Leu Gly Ala Thr Thr Leu Arg Lys Ala Gly Ile Pro
            185                 190                 195 att cag ctg gtaagtcatc ccttgtcaac ttatgcaagg gcgcaatggg            789
Ile Gln Leu
       200 actaattgat tgtgaag tat aat tac gga tcc ccc cgt gtt gga aac acg    839
                Tyr Asn Tyr Gly Ser Pro Arg Val Gly Asn Thr
                                205                 210 gcc ttg gca aca tac atc acc gca cag ggt ccc aat tac cgt gtc aca    887
Ala Leu Ala Thr Tyr Ile Thr Ala Gln Gly Pro Asn Tyr Arg Val Thr
            215                 220                 225 cac aca aac gat att gtg ccc aga ctc ccg ccc caa gct ttt ggc ttc    935
His Thr Asn Asp Ile Val Pro Arg Leu Pro Pro Gln Ala Phe Gly Phe
            230                 235                 240 agc cac ctt agc ccg gag tac tgg atc acg agc ggc gac aac gtg cct    983
Ser His Leu Ser Pro Glu Tyr Trp Ile Thr Ser Gly Asp Asn Val Pro
245                 250                 255 gtc acg acg tct gat atc acg gtc atc cag gga atc gac tca gac gct   1031
Val Thr Thr Ser Asp Ile Thr Val Ile Gln Gly Ile Asp Ser Asp Ala
260                 265                 270                 275 gga aat tcg gga gag gat atc acc agc atc gag gcc cat aat tgg tat   1079
Gly Asn Ser Gly Glu Asp Ile Thr Ser Ile Glu Ala His Asn Trp Tyr
                280                 285                 290 ctc ggc gat att gat gct tgt caa tgagactata agcggagtat ataacagctt  1133
Leu Gly Asp Ile Asp Ala Cys Gln
            295 tggatagtat aaagggcca gtacacttgg gctaacgcat gaggaatgac attgatgacc   1193 tatcttgcca atgcaatcag tttataagg agagtcctca tgattgatta tgtcaattgg   1253 tatggagtag aaataaactg tacagatctc tggatccgcc gagtggacat tcattatgag   1313 gttctgggga agtttgtttg gtttggactt tgacacctgg agtttatccc catctccatc   1373 aactcgtctg attgtggctc gacgagcgca ttcttactga atgctcatct gtttgaatag   1433 aatatgatta acgagcagta actcccattc ctttcgaacg cctttgcgca attgaatcca   1493 tccttccaac ccgtgcaact tcaaccagcc gcccgggcga ctctgcgcat tctcaacatc   1553
```
tctcgacccg ccgcgatggt cgctgctcca tgctgctgat actcttctgt tatcagtaat    1613
cacggaaatt gtcata    1629

<210> SEQ ID NO 2
<211> LENGTH: 299
<212> TYPE: PRT
<213> ORGANISM: Aspergillus fumigatus

<400> SEQUENCE: 2

Met Val Gln Phe Lys Ser Val Arg Thr Leu Ala Val Ala Ala Phe Ala
1               5                   10                  15

Ala Leu Gly Ala Ala Pro Ala Gly Leu Ala Glu Arg Asp Val Ser
            20                  25                  30

Ala Ser Val Leu Gln Lys Leu Ser Leu Phe Ala Gln Tyr Ser Ala Ala
        35                  40                  45

Ala Tyr Cys Thr Asn Asn Ile Asn Ser Thr Gly Thr Lys Leu Thr Cys
    50                  55                  60

Ser Ala Gly Asn Cys Pro Leu Val Glu Ala Ala Asn Thr Lys Thr Leu
65                  70                  75                  80

Ala Glu Phe Tyr Glu Ala Gly Ser Ser Glu Ser Phe Gly Asp Thr Ala
                85                  90                  95

Gly Phe Leu Val Ala Asp Thr Thr Asn Lys Leu Leu Val Val Ser Phe
            100                 105                 110

Arg Gly Ser Arg Thr Ile Asp Asn Trp Ile Ala Asn Leu Asp Phe Val
        115                 120                 125

Leu Asp Ser Val Ser Asp Ile Cys Ser Gly Cys Ala Ala His Gly Gly
    130                 135                 140

Phe Trp Lys Ser Trp Glu Val Val Ala Asn Ser Leu Thr Thr Glu Leu
145                 150                 155                 160

Asn Ser Ala Val Asn Thr Tyr Pro Gly Tyr Thr Ile Val Phe Thr Gly
                165                 170                 175

His Ser Leu Gly Ala Ala Leu Ala Thr Leu Gly Ala Thr Thr Leu Arg
            180                 185                 190

Lys Ala Gly Ile Pro Ile Gln Leu Tyr Asn Tyr Gly Ser Pro Arg Val
        195                 200                 205

Gly Asn Thr Ala Leu Ala Thr Tyr Ile Thr Ala Gln Gly Pro Asn Tyr
    210                 215                 220

Arg Val Thr His Thr Asn Asp Ile Val Pro Arg Leu Pro Pro Gln Ala
225                 230                 235                 240

Phe Gly Phe Ser His Leu Ser Pro Glu Tyr Trp Ile Thr Ser Gly Asp
                245                 250                 255

Asn Val Pro Val Thr Thr Ser Asp Ile Thr Val Ile Gln Gly Ile Asp
            260                 265                 270

Ser Asp Ala Gly Asn Ser Gly Glu Asp Ile Thr Ser Ile Glu Ala His
        275                 280                 285

Asn Trp Tyr Leu Gly Asp Ile Asp Ala Cys Gln
    290                 295

<210> SEQ ID NO 3
<211> LENGTH: 16
<212> TYPE: PRT
<213> ORGANISM: Aspergillus fumigatus

<400> SEQUENCE: 3

Asp Val Ser Ala Ser Val Leu Gln Lys Leu Ser Leu Phe Ala Gln Tyr

-continued

```
<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agagtctgcc tatattctct ctgaaagg                                        28

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tatgacaatt tccgtgatta ctg                                             23
```

CLONING, EXPRESSION AND USE OF ACID PHOSPHOLIPASES

RELATED APPLICATIONS

This application is a divisional of, and claims priority under 35 U.S.C. §120 to, U.S. patent application Ser. No. 13/502,945 filed Apr. 19, 2012, which is a national stage application, filed under 35 U.S.C. §371, of International Application No. PCT/EP2010/066234 filed Oct. 27, 2010, which claims the benefit under 35 U.S.C. §119 to German Patent Application No. 102009051013.3, filed Oct. 28, 2009, the entire contents of each of which are hereby incorporated herein by reference in their entirety.

The invention relates to new DNA sequences which code for polypeptides having phospholipase activity essentially without lipase activity. The invention further relates to new polypeptides having phospholipase activity essentially without lipase activity. These polypeptides are acid phospholipases with low molecular weight, high thermostability and high temperature resistance. Furthermore, these polypeptides are active within a broad pH range. Moreover, the invention also relates to the use of these phospholipases for reducing phosphorus-containing compounds, for example in the production of edible oils, as well as to the use of these phospholipases as bakery improver, animal feed additive, additive in the processing of textile raw materials, etc.

Crude vegetable oils contain associated material (such as free fatty acids, phospholipids, heavy metals, colorants . . . ) which affect the quality and shelf life of the oil and complicate its further processing due to the hydrolytic and oxidative modification of lipids during storage. Therefore, it is necessary to refine the crude vegetable oils after their extraction in order to remove the impurities. In the production of high-quality edible oils the refining process comprises the steps of degumming, bleaching and deodorization.

The first step in the process of refining oils is degumming. During the degumming process gummy substances, primarily phospholipids, are removed which negatively affect the taste of the oil and which disturb the further steps of the oil refining process.

Since the phosphorous content is an indicator for the degree of degumming the quality of the degummed oil obtained may be assessed by determining the content of the remaining phosphorus. For the further steps of the refining process degummed oil with a content of the remaining phosphorus of less than 10 ppm is required.

Phospholipids are complex, phosphorus-containing lipids. Phospholipids, such as phosphatidyl choline or lecithin, consist of a glycerine structure which is esterfied with fatty acids at positions sn-1 and sn-2 and with an ester-bound phosphate group at position sn-3. The phosphate group itself may be esterfied with e.g. a primary alcohol group. At positions sn-1 and sn-2 natural phospholipids contain different fatty acid chains which, in the case of plants, are primarily polyunsaturated acyl chains. There are two kinds of phospholipids: hydratable ones and non-hydratable ones. In order to remove the phospholipids different methods are used.

The simplest method is water-degumming. During this process hydratable phospholipids may be washed out with the help of water and are thus removed from the oil. Depending on the type and quality of the crude oil the degummed oil still contains 80 to 200 ppm of phosphorus after this process.

In the acid degumming process the oil is treated with acid. The acid transforms non-hydratable phospholipids into hydratable phospholipids. The hydratable phospholipids become oil-insoluble. An oil-insoluble slurry is formed which is removed from the oil by means of centrifugation or filtration. After this process the content of the remaining phosphorus in the oil is approximately 25 to 100 ppm.

Enzymatic degumming offers an efficient, cost-effective and environmentally friendly process for gently removing phospholipids from edible oil.

Phospholipases are enzymes which cleave phospholipids and are divided according to their enzymatic cleavage sites at the phospholipid into acylhydrolases (phospholipase A1, A2 and B) and phosphodiesterases (phospholipase C and D). The phospholipase A1 (EC 3.1.1.32) hydrolyzes the fatty acid at the sn-1 position of phospholipid molecules and the phospholipase A2 (EC 3.1.1.4) specifically cleaves the sn-2 ester bond from the phospholipid. As reaction products the lysophospholipid and the free fatty acid are formed. Phospholipase B (EC 3.1.1.5) unspecifically cleaves the fatty acid at both sn-1 and sn-2 positions. Phospholipase C (EC 3.1.4.10) hydrolyzes the phosphate ester bond between glycerine and the phosphate group to form phosphate monoester and diacylglycerol. Phospholipase D (EC 3.1.4.4) catalyzes the hydrolysis of the terminal phosphodiester bond to form the cleavage products phosphatidic acid and choline.

The extraction of phospholipase A2 from bovine and porcine pancreas and from the toxin of honeybees or several snake species is already known. Phospholipase may also be extracted from microorganisms such as bacteria and fungi and may be produced with a sufficient yield by means of recombinant techniques.

In patent EP 0 513 709 an efficient enzymatic degumming process is presented for the first time. The new process uses the enzyme phospholipase A2 for the first time which cleaves the fatty acid at position sn-2 of phospholipids. The process was tested with soybean and rapeseed oil having a phosphorus content of 72 to 110 ppm. The reaction batch contained up to 5 wt. % (w/w) water in relation to the oil and was incubated at a pH value of 5.0 to 5.5 at 40° C. or alternatively 60° C. for up to 5 hours. The lysophospholipid produced may be removed from the oil by means of centrifugation. After the process the content of the remaining phosphorus in the degummed oil is less than 5 ppm.

During the degumming process the oil is mixed with a defined amount of water. Then, the enzyme-containing aqueous phase and the oily phase are mixed in order to allow the enzyme to act. The amount of water should hereby be as small as possible. The use of large amounts of water leads to increased energy consumption and increased disposal costs. Therefore the process of enzymatic degumming with a low water content (2%) is already advantageous in this regard.

In US2007/134777 it is stated that the enzymatic degumming of vegetable oil with the help of phospholipase A1 is carried out at a pH value of between 4.0 and 5.0. The optimal pH value for carrying out this process is between 4.5 and 5.0. In this pH range the released calcium and/or magnesium ions may combine with other chemicals (anions) of the reaction buffer to form hardly soluble salts which deposit on the surface of the reactors and thus soil the device. The removal of such soiling and the cleaning of the device is laborious. In order to reduce the soiling of the interior of the device the reaction is preferably carried out at a pH value of approximately 4. However the enzyme becomes less active or functionally inactive if the pH value of the reaction is lowered further.

EP 0 904 357 describes that in *Aspergillus niger* a phospholipase A was found for the degumming of edible oil.

WO2008/040466 describes that a phospholipase having a molecular weight of 65 kDa may be used in *Aspergillus*

*fumigatus* for the degumming of edible oil with a water content of 5% at temperatures of up to 65° C.

EP 1 788 080 describes the use of phospholipase C of *Bacillus cereus* for the degumming of oil in 6 hours at 60° C. with a water content of 15% in relation to the oil. After the process the content of the remaining phosphorus is less than 5 ppm.

In WO2008/094847 it is described that the reaction time of the oil degumming process may be reduced to 30 min under the reaction of the phospholipase A1 or A2 with the phospholipase C, respectively.

Phospholipases are also manifoldly used in the food industry and the animal feed industry, e.g., for the preparation of dough, for the preparation of bakery products, for increasing the yield of cheese production etc. Thus, there is a need for phospholipases which may be versatilely used in technology.

In biotechnology phospholipases are used as biocatalysts for the extraction of phospholipids. Phospholipids are polar lipids and act as emulgators due to their lipophilic and hydrophilic structural features. Examples are the use of phospholipases in the production of modified lecithins, as food emulsions in the production of sauces, mayonnaise and salad dressing, in the production of instant powders, such as milk, cocoa and coffee powders, as flow improvers in the production of chocolate and as food supplements. In pharmaceutical and cosmetic industry phospholipids and lysophospholipids are used for the production of cremes, lotions, gels and liposome formulations.

Lecithin is also required for the production of varnishes, paints, magnetic tapes, speciality papers, leather and textiles. Phospholipases are also used in textile industry for "bioscouring" to clean the plant fibre before further process steps such as colorization are carried out. A mixture of phospholipase together with other enzymes may also be used here. The other enzymes may be selected from the group of cellulases, hemicellulases, pectinases, proteases and oxidoreductases.

Thus there is a constant need for phospholipases having a possibly large and optimized field of application in the art.

The present invention is therefore based on the object of providing proteins or polypeptides with improved phospholipase properties. The new phospholipases are particularly not to show lipase activity relevant in technological processes. In particular, the proteins having phospholipase activity are to be active over a large pH range and are to be highly temperature-resistant.

Moreover, the production of the proteins having phospholipase activity is to be simple, cost-efficient and commercial. Furthermore, expression constructs according to the invention which are suitable for the production of the proteins having phospholipase activity are to be provided.

Figure 7:
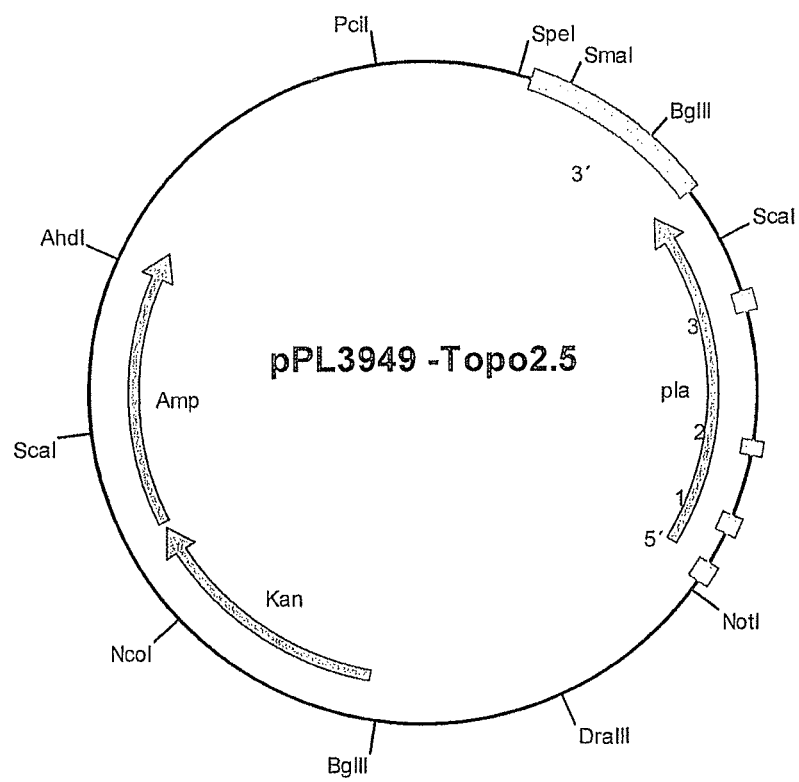

The aforementioned objects are solved by means of a DNA sequence, which codes for a polypeptide having phospholipase activity essentially without lipase activity, characterized in that the DNA sequence is selected from a) DNA sequences that comprise a nucleotide sequence according to SEQ ID NO: 1, b) DNA sequences that comprise the coding sequence according to SEQ ID NO: 1, c) DNA sequences that code for the protein sequence according to SEQ ID NO: 2, d) DNA sequences that are coded for by the plasmid pPL3949-Topo2.5 with the restriction map according to FIG. 7, which is deposited under accession number DSM 22741, e) DNA sequences that hybridize under stringent conditions with one of the DNA sequences according to a), b), c) or d), f) DNA sequences that are related to the DNA sequences according to a), b), c), d) or e) due to the degeneration of the genetic code, and g) complementary strands to the sequences according to a) to f).

The invention further relates to a polypeptide having phospholipase activity essentially without lipase activity selected from a) a polypeptide which is coded for by the coding part of a DNA sequence as defined above, b) a polypeptide having the sequence according to SEQ ID NO: 2 or a sequence derived therefrom, which may be obtained by substitution, addition, deletion of one or more amino acids, c) a polypeptide having a sequence that has at least 83% identity with the amino acids 1 to 299 of SEQ ID NO: 2, d) a polypeptide which is coded for by a nucleic acid sequence which hybridizes under stringent conditions with (i) nucleotides 55 to 1106 of SEQ ID NO: 1, (ii) the cDNA sequence contained in nucleotides 55 to 1106 of SEQ ID NO: 1, (iii) a partial sequence of (i) or (ii) composed of at least 100 nucleotides, or (iv) a complementary strand of (i), (ii) or (iii), e) a variant of the polypeptide having SEQ ID NO: 2, comprising a substitution, deletion and/or insertion of one or more amino acids, f) allelic variants to amino acid sequences a) to e).

Furthermore, the invention relates to expression constructs or hosts that are able to express polypeptides having phospholipase activity according to the invention. Moreover, the invention also relates to the respective expression plasmids and vectors. Furthermore, the invention relates to processes for the degumming of vegetable oil using the polypeptides according to the invention as well as to the use of the polypeptides according to the invention in the field of food technology, in particular for the preparation of dough, bakery products or dairy products or in animal nutrition and in the processing of textile raw materials, the so-called scouring or bioscouring.

According to a further embodiment the invention relates to a polypeptide having phospholipase activity essentially without lipase activity characterized in that it has a molecular weight in the range of 28 to 30 kDA and preferably of approximately 28.6 kDa, a broad pH optimum and a high temperature resistance and that it may be isolated from an organism of the genus *Aspergillus*.

High temperature resistance in this context means that after 6 hours at a temperature of 60° C. under the conditions of the oil degumming process with a low water content of 2% the enzyme retains its activity to an industrially exploitable extent. The enzyme retains its activity to an industrially exploitable extent if it produces oils of which the contents of the remaining phosphorus are technologically insignificant, so to speak. Preferably the content of the remaining phosphorus in the enzymatically degummed oil is less than 10 ppm, more preferably less than 5 ppm.

Surprisingly it was found that a DNA sequence which codes for a polypeptide having phospholipase activity essentially without lipase activity which has a low molecular weight as well as a high temperature resistance may be isolated from a strain of the genus *Aspergillus fumigatus*. This phospholipase is an acid phospholipase derived from a filamentous fungus with a calculated molecular weight of approximately 28.6 kDa, which is able to hydrolyze at least one of the two fatty acids from lecithin.

In contrast to the polypeptides having phospholipase activity known from the state of the art, the phospholipases according to the invention have a high temperature resistance (at 60° C.) and can, thus, also be beneficially used in processes of enzymatic degumming with a low water content of 2% (in relation to oil) and at a pH value of 4.0. This is of particular economic interest since the temperature of the oil does not first have to be lowered in the degumming processes to make enzymatic degumming without inactivation of the enzyme possible, and subsequently the temperature of the oil has again to be increased in order to decrease the viscosity of the oil for the centrifugation step used for separating the oily phases from the aqueous phases. The temperature resistance of the polypeptides having phospholipase activity according to the invention is also advantageous for other applications in the field of food technology and animal nutrition and in textile processing, respectively.

Phospholipases known from the state of the art are excluded from the scope of the invention.

Therefore it is particularly advantageous that the phospholipases derived from *A. fumigatus* according to the invention are active within a large pH range of 3 to 5 or show a broad activity optimum within this range. Therefore the phospholipases according to the invention do not only have the advantage that they essentially have no lipase activity. They additionally develop their enzyme activity over a large pH range and may thus be used over a large pH range.

Enzymes having phospholipase activity (phospholipase A, B, C or D) from *Aspergillus fumigatus* have so far been mentioned in several publications (Birch et al., Comparison of extracellular phospholipase activities in clinical and environmental *Aspergillus fumigatus* isolates, 2004, Med Mycol 42(1): 81-86; Rementeria et al., Genes and molecules involved in *Aspergillus fumigatus* virulence, 2005, Rev Iberoam Micol 22(1): 1-23) but have not been exactly characterized. From the genome sequence of *Aspergillus fumigatus* (Nierman et al., Genomic sequence of the pathogenic and allergenic filamentous fungus *Aspergillus fumigatus*, 2005, Nature, 438(7071): 1151-6) several hypothetical phospholipase (A, B, C, D) and lysophospholipase genes were derived under the term "conceptual translation". Thus, e.g. one hypothetical phospholipase A having 241 amino acids and three lysophospholipases Plb1, Plb2 and Plb3 having a high molecular weight were displayed. Furthermore, the database shows a small hypothetical extracellular lipase having 299 amino acids and a calculated molecular weight of approximately 28.5 kDa (GenBank EAL86100) as well as several lipases having between 409 and 587 amino acids.

Shen et al. (Characterisation and expression of phospholipase B from the opportunistic fungus *Aspergillus fumigatus*, 2004, FEMS Microbol Lett 239(1): 87-93) succeeded in cloning and characterizing 3 phospholipase B genes from *Aspergillus fumigatus*. The secreted proteins AfPL1 having 633 amino acids and AfPL3 having 630 amino acids have a molecular weight of approximately 68 kDa. The protein AfPL2 is a cytosolic protein having 588 amino acids and has a molecular weight of approximately 63 kDa.

Moreover, a phospholipase having 633 amino acids (WO2008/040466) and a lysophospholipase having 611 amino acids (WO2008/040465) were isolated from *Aspergillus fumigatus* RH3949.

Furthermore, an acid phospholipase (pI 4.1) having a small molecular weight within the range of 28 to 30 kDa was found in the genome of *Aspergillus fumigatus* RH3949.

In the protein sequencing process of this "small" phospholipase the first 16 amino acids showed 93% identity at the N-terminus with the N-terminal sequence of the hypothetical extracellular lipase having 299 amino acids (GenBank EAL86100) from *Aspergillus fumigatus* Af293. The identity of the mature (AA 30-299) sequence of the "small phospholipase" from RH3949 with the sequence of the hypothetical extracellular lipase, however, is only approximately 82%. This was particularly surprising since at a comparable site in the genome of a further *Aspergillus fumigatus* strain (A1163) a sequence having a significantly higher identity with the hypothetical lipase from Af293 had been found (GenBank EDP1054) (Fedorova et al., Genomic Islands in the Pathogenic Filamentous Fungus *Aspergillus fumigatus*, 2008, PloS Genet. 4. e1000046).

In contrast thereto there is no analogy between two N-terminal phospholipase sequences from *Aspergillus fumigatus* Af293 (phospholipase A having 241 amino acids, GenBank EAL85761) and *Aspergillus fumigatus* RH3949 (phospholipase having pI 4.1).

Therefore the phospholipase according to the invention differs from known phospholipases from *Aspergillus fumigatus* as well as from sequences annotated as lipases of closely related *Aspergillus fumigatus* strains such as Af293.

According to the invention several oligonucleotide primers were derived and synthesized from the DNA sequence data (GenBank AAHF01000011) for the hypothetical extracellular lipase (GenBank EAL86100).

Surprisingly it was found that the DNA sequence according to the invention could be isolated from the *Aspergillus* strain RH3949 by means of primers derived from the genome sequence of the strain Af293 (cf. example 4). This was not expected since the strain RH3949 (an environmental isolate) used for amplification differs from Af293 (clinical isolate) phenotypically and therefore most probably also genotypically (sequence). Thus, it was not possible either to amplify the phospholipase gene from RH3949 by means of other primer pairs having bonding sites adjacent to N2-3948 and ApaI-3949 on the genomic DNA of the strain Af293.

The amplification of the gene was carried out with the help of the polymerase chain reaction (PCR) from genomic DNA of *Aspergillus fumigatus* RH3949.

The temperature resistance and the broad pH optimum of the phospholipase according to the invention were surprising and not to be expected on the basis of the phospholipases described in the state of the art. For none of the naturally occurring phospholipases derived from filamentous fungi as described in the state of the art have these properties been described or merely suggested.

The phospholipase sequence according to SEQ ID NO: 2 according to the invention was compared to phospholipase sequences of the state of the art. A partial analogy of the amino acid sequence was found with known amino acid sequences from other *Aspergillus* strains, i.e. an analogy of 60% with a lipase of *Aspergillus tubingensis* (WO98/45453) or with a lysophospholipase from *Aspergillus foetidus* (EP0808903), 59% with an *Aspergillus niger* phospholipase (WO03/097825, WO98/31790).

The sequence SEQ ID NO: 2 exhibits the highest identity of 82% with a hypothetical sequence for extracellular lipase (GenBank EAL86100) from *Aspergillus fumigatus* Af293 (Nierman et al., Genomic sequence of the pathogenic and allergenic filamentous fungus *Aspergillus fumigatus*, 2005, Nature, 438(7071): 1151-6).

Surprisingly, under the conditions of the enzymatic degumming of edible oil the phospholipase isolated from *Aspergillus fumigatus* RH3949 according to the invention does not show any lipase activity relevant for this process. Furthermore, this enzyme has a remarkably broad pH optimum and a high temperature resistance in contrast to phospholipases from other *Aspergillus* strains known so far. Thus, the enzyme according to the invention may be used advantageously in a process of enzymatic degumming of edible oils since it does not hydrolyze any or merely insignificant portions of triglyceridebonds in the oil.

Moreover, the invention also relates to polypeptides having phospholipase activity essentially without lipase activity with a sequence which has an identity of at least 83% with the sequence according to SEQ ID NO: 2. Preferably the invention relates to a polypeptide having phospholipase activity with a sequence which has an identity of at least 83% with the amino acids 1 to 299 of SEQ ID NO: 2. Preferably the degree of identity with the amino acids 1 to 299 of SEQ ID NO: 2 is at least 90%, more preferably at least 95%, even more preferably at least 97% and particularly preferably at least 98% provided that the respective sequences have phospholipase activity essentially without lipase activity.

The polypeptides having phospholipase activity according to the invention do not have any significant lipase activity or are rather essentially without lipase activity. The polypeptides according to the invention essentially do not have any lipase activity disadvantageous for industrial processes of oil degumming, i.e. the polypeptides according to the invention essentially do not show any activity against lipolytically cleavable compounds in the oil to be degummed. This means that under the conditions of the enzymatic degumming of edible oil the phospholipases according to the invention do not have any lipase activity relevant for this process. Technologically speaking this means that polypeptides having phospholipase activity according to the invention hydrolyze p-nitrophenyl palmitate as lipase substrate only to an insignificant and/or undetectable extent. For the polypeptides having phospholipase activity according to the invention the ratio of phospholipase activity to lipase activity is preferably >1000:1, more preferably 5000:1 to 10000:1, even more preferably 7000:1 and most preferably 7500:1.

The degree of sequence identity is preferably determined in such a way that the number of residues of the shorter sequence which is involved in the comparison and has a "corresponding" counterpart in the other sequence is determined. For the purposes of the present invention the identity is preferably determined in the usual manner by using the usual algorithms. According to the invention only the cDNAs or amino acids of the respective mature proteins are used for the comparison. Similar, preferably identical sequence counterparts were determined according to the invention as homologue sequences by means of known computer programs. An example of such a program is the program Clone Manager Suite, which includes the program part Align Plus and is distributed by Scientific & Educational Software, Durham, N.C., U.S.A. A comparison of two DNA sequences or amino acid sequences as defined above is thereby carried out under the option local alignment either according to the FastScan-MaxScore method or according to the Needleman-Wunsch method, keeping the default values. The program version "Clone Manager 7 Align Plus 5" with the functions "Compare Two Sequences/Local Fast Scan-Max Score/Compare DNA sequences" or for amino acids "Compare Two Sequences/Global/Compare sequences as Amino Acids" was particularly used to calculate the identity according to the invention. The algorithms made available from the following sources were thereby used: Hirschberg, D. S. 1975. A linear space algorithm for computing maximal common subsequences. Commun Assoc Comput Mach 18:341-343; Myers, E. W. and W. Miller. 1988. Optimal alignments in linear space. CABIOS 4:1, 11-17; Chao, K-M, W. R. Pearson and W. Miller. 1992. Aligning two sequences within a specified diagonal band. CABIOS 8:5, 481-487.

The invention further relates to addition molecules and/or deletion molecules of the aforementioned polypeptides having phospholipase activity. Thus, a polypeptide having phospholipase activity modified according to the invention may be elongated by adding further sequences at the N-terminal and/or C-terminal end, whereby the thus obtained amino acid sequences still have to show phospholipase activity essentially without lipase activity. Thereby hybrid molecules may be produced which have further advantageous properties. For example, suspension proteins or their native precursor forms may be added to largely secreted proteins, which further enhances secretion efficiency. Moreover, active sequence segments of other enzymes may be added to produce enzymes with multiple specificity. Furthermore, polar and non-polar sequences may be added to specifically influence the solubility properties or the membrane mobility of the thus obtained enzyme.

Sequence segments of the polypeptide having phospholipase activity may also be deleted according to the invention, keeping the phospholipase activity essentially without lipase activity. The mutations, elongations and shortenings may be carried out in a way known per se and with the help of methods well known in the state of the art. Shortened polypeptides are often characterized by an enhanced secretion height compared to the full-length polypeptides. They may also show higher thermostabilities compared to the full-length polypeptide since they only contain the "compressed core".

The production of such variants is generally known in the state of the art. For example, amino acid sequence variants of the polypeptides may be produced by mutation in the DNA. Processes for mutagenesis and changes in the nucleotide sequence are well known in the state of the art (cf. for example Tomic et al. NAR, 18:1656 (1990), Giebel and Sprtiz NAR, 18:4947 (1990)).

Details on appropriate amino acid substitutions which do not negatively influence the biological activity of the protein of interest can be found in the model by Dayhoff et al., Atlas of Protein Sequence and Structure, Natl. Biomed. Res. Found., Washington, D.C. (1978). Conservative substitutions such as the substitution of an amino acid by another one with similar properties are preferred. These substitutions may be divided into two main groups with altogether four subgroups, and a substitution in each subgroup is referred to as conservative substitution, which does preferably not influence the activity or the folding of the protein.

| aliphatic | non-polar | G A P |
| | | I L V |
| | polar and uncharged | C S T M N Q |
| | polar and charged | D E |
| | | K R |
| aromatic | | H F W Y |

The expressions "protein", "peptide" and "polypeptide" are essentially used interchangeably. A polypeptide or enzyme having phospholipase activity or a phospholipase is to refer to an enzyme which catalyzes the release of fatty acids from phospholipids, for example, lecithins. The phospholipase activity may be determined by means of the use of any measuring method known per se in which one of these substrates is used.

In connection with the polypeptides according to the invention the expressions "phospholipase" or phospholipase A are to refer to enzymes having phospholipase A1 activity as well as phospholipase A2 activity. Phospholipase A1 or A2 is thereby defined according to the standard enzyme EC classification as EC 3.1.1.32 or 3.1.1.4, respectively.

Phospholipase B or lysophospholipase are polypeptides according to the standard enzyme EC classification EC 3.1.1.5.

The invention also relates to DNA sequences which code for a polypeptide having phospholipase activity, comprising mutations, modifications or variations of the sequence according to SEQ ID NO: 1. Furthermore, the invention also relates to sequences which hybridize with the aforementioned sequences under relaxed or stringent conditions. The following conditions are considered as stringent: hybridization at 65° C., 18 h in dextran sulphate solution (Genescreen-Plus, DuPont), subsequent washing of the filter for 30 min, respectively, at first with 6×SSC, twice 2×SSC, twice 2×SSC, 0.1% SDS and finally with 0.2×SSC at 65° C. (membrane transfer and detection methods, Amersham).

Furthermore, the invention also relates to DNA sequences which are related to the aforementioned sequences according to the invention due to the degeneration of the genetic code as well as allelic variants thereof. The degeneration of the genetic code may thereby result from the natural degeneration or an especially selected codon usage. Naturally occurring allelic variants may be identified by means of well-known techniques of molecular biology such as the polymerase chain reaction (PCR) and hybridization techniques.

The invention also relates to a process for the production of a polypeptide having phospholipase activity using recombinant techniques comprising the growing of recombinant prokaryotic and/or eukaryotic host cells which comprise a DNA sequence according to the invention under conditions which promote the expression of the enzyme as well as the subsequent extraction of the enzyme. The invention further relates to the use of the polynucleotide sequences according to the invention for the production of probes for the detection of similar sequences which code for corresponding enzymes in other organisms as well as for the transformation of host cells.

A DNA sequence which codes for a polypeptide according to the invention may be used to transform any host cells such as cells of fungi, yeasts, bacteria, plants or mammals. Cells transformed in such a way are characterized by a secretion of the phospholipase according to the invention. The thus produced phospholipase enzyme effects an efficient hydrolysis of the fatty acids from phospholipids.

The invention also relates to expression cassettes which may be used for introducing the DNA sequence coding for a phospholipase according to the invention or an open reading frame into a host cell. They preferably comprise a transcription start region which is connected with the open reading frame. Such an expression cassette may comprise a variety of restriction cleavage sites for inserting the open reading frame and/or other DNAs, e.g., a transcription regulator region and/or selectable marker genes. The transcription cassette comprises in 5→3' direction of the transcription a transcription start region and a translation start region, the DNA sequence of interest and a transcription stop region and translation stop region that is functional in a microbial cell. The termination region may be native regarding the transcription initiation region, may be native regarding the DNA sequence of interest or may be derived from any other source.

The expression "open reading frame" (ORF) refers to the amino acid sequence which is coded for between the translation start codons and translation stop codons of a coding sequence. The expressions "start codon" and "stop codon" refer to a unit of three adjacent nucleotides (codons) in a coding sequence which specify the chain start and chain stop of the protein synthesis (mRNA translation).

In connection with a nucleic acid "operative linkage" refers to a compound as part of the same nucleic acid molecule in an appropriate position and orientation to the transcription start of the promoter. DNA in functional connection to a promoter is located under the transcription initiation regulation of the promoter. Coding sequences may be operatively linked with the regulator sequence in sense orientation or antisense orientation. Regarding polypeptides, operative linkage refers to the connection as part of the same polypeptide, i.e., via peptidyl bonds.

According to the invention any promoter may be used. Promoter usually refers to the nucleotide sequence upstream (5') to the coding sequence and controls the expression of the coding sequence by providing the recognition of the RNA polymerase and other factors which are necessary for the correct transcription. The promoter used according to the invention may comprise a minimal promoter, i.e., a short DNA sequence from a TATA box and other sequences which specify the transcription start site to which regulator elements are attached for expression control.

The promoter used according to the invention may also comprise a nucleotide sequence which comprises a minimal promoter and regulator elements, and may control the expression of a coding sequence or functional RNA. This type of promoter sequence consists of proximal and distal elements located upstream, whereby the elements named last are often referred to as enhancers. Consequently, an enhancer is a DNA sequence which may stimulate the promoter activity and may be an element inherent to the promoter or an inserted heterologous element to improve the expression height or tissue specificity of a promoter. It may work in both orientations and may even work if it is located upstream or downstream to the promoter. Not only enhancers but also other upstream located promoter elements sequence-specifically bind DNA-binding proteins mediating their effects. Promoters may be derived from a native gene in their entirety or may be composed of different elements derived from different naturally occurring promoters or may even be composed of synthetic DNA segments. A promoter may also comprise DNA sequences which are involved in the binding of protein factors which control the efficiency of the transcription initiation as response to physiological or development-related conditions.

Promoter elements, particularly TATA elements which are inactive or have a strongly reduced promoter activity in the absence of an upstream activation are referred to as minimal promoters or core promoters. In the presence of an appropriate transcription factor or appropriate transcription factors the function of the minimal promoter is the enabling of the transcription. Thus, a minimal promoter or core promoter only consists of all basic elements which are necessary for the transcription initiation, e.g., a TATA box and/or an initiator.

The invention also relates to vector constructs comprising DNA sequences according to the invention. These vector constructs comprise any plasmid, cosmid, phage or other vector in double-stranded or single-stranded, linear or circular form, which might be transmittable or mobilizable themselves and may either transform a prokaryotic or eukaryotic host by means of integration into the cellular genome or are extra-chromosomally present (e.g., autonomously replicating plasmids with replication origin).

Vectors, plasmids, cosmids, artificial yeast chromosomes (YACs), artificial bacterial chromosomes (BACs) and DNA segments to be used for the transformation of cells generally comprise the DNA which codes for the phospholipase according to the invention as well as another DNA such as cDNA, a gene or genes which is/are to be introduced into the cells. These DNA constructs may comprise further structures such as promoters, enhancers, polylinkers or also regulator genes, if necessary. One of the DNA segments or genes which was/were selected for the cellular introduction conveniently codes/code for a protein which is expressed in the thus obtained transformed (recombinant) cells, which leads to a screenable or selectable property and/or provides the transformed cell with an improved phenotype.

The construction of vectors which may be used according to the invention is known to a person skilled in the art due to the aforementioned disclosure and the general expert knowledge (cf., e.g., Sambrook et al., Molecular Cloning: A Laboratory Manual (2nd ed., Cold Spring Harbor Laboratory Press, Plainview, N.Y. (1989))).

The expression cassette according to the invention may comprise one or several restriction site(s) to put the polynucleotide coding for the phospholipase under the control of a regulator sequence. The expression cassette may also comprise a termination signal in operative linkage with the polynucleotide as well as regulator sequences which are required for the proper translation of the polynucleotide. The expression cassette which comprises the polynucleotide according to the invention may be chimeric, i.e., at least one of its components is heterologous in relation to at least one of the other components. The expression of the polynucleotide in the expression cassette may be under the control of a constitutive promoter, an inducible promoter, a regulated promoter, a viral promoter or a synthetic promoter.

The vectors may already comprise regulator elements, e.g., promoters, or the DNA sequences according to the invention may be manipulated in such a way that they comprise such elements. Appropriate promoter elements which may be used are known in the state of the art and are, for example, for *Trichoderma reesei* the cbh1 promoter or cbh2 promoter, for *Aspergillus oryzae* the amy promoter, for *Aspergillus niger* the xyl promoter, glaA promoter, alcA promoter, aphA promoter, tpiA promoter, gpdA promoter, sucI promoter and pkiA promoter. Appropriate promoter elements which may be used for expression in yeast are known in the state of the art and are, for example, the pho5 promoter or the gap promoter for expression in *Saccharomyces cerevisiae* and for *Pichia pastoris*, for example, the aoxI promoter or the fmd promoter, or the mox promoter for *H. polymorpha*.

DNA which is appropriate for introduction into cells may also comprise, besides the DNA according to the invention, DNA which was derived or isolated from any source. An example of a derived DNA is a DNA sequence which was identified in a given organism as a useful fragment and then chemically synthesized in a basically purified form. An example of such a DNA is an appropriate DNA sequence which was, for example, obtained by the use of restriction endonucleases, so that it may be further manipulated, for example, amplified according to the invention. The amdS gene from *Aspergillus nidulans*, which may be used as a marker gene, and its regulatory sequences as well as polylinkers are among those, inter alia.

Such a DNA is usually referred to as recombinant DNA. Thus, an appropriate DNA comprises completely synthetic DNA, semi-synthetic DNA, DNA isolated from biological sources and DNA derived from introduced RNA. Generally, the introduced DNA is no original part of the genotype of the recipient DNA, however, according to the invention, a gene may also be isolated from a given genotype and optionally altered and subsequently multiple copies of the gene may be introduced into the same genotype, e.g., to increase the production of a given gene product.

The introduced DNA comprises without limitation DNA from genes such as from bacteria, yeasts, fungi or viruses. The introduced DNA may comprise modified or synthetic genes, parts of genes or chimeric genes including genes of the same or a different genotype. This may also include for example DNA of the plasmids pUC18, pUC19.

The DNA used according to the invention for the transformation may be circular or linear, double-stranded or single-stranded. In general, the DNA is a chimeric DNA such as a plasmid DNA, which also comprises coding regions which are flanked by regulator sequences and support the expression of the recombinant DNA present in the transformed cell. For example, the DNA itself may comprise or consist of a promoter that is active in a cell, that is derived from a source differing from the cell, or a promoter that is already present in the cell, i.e., the transformation target cell, may be used.

In general, the introduced DNA is relatively small, less than about 30 kb, in order to minimize the sensitivity to physical, chemical or enzymatic degradation, which increases with the size of the DNA.

The selection of an appropriate expression vector depends on the host cells. Yeast expression vectors or fungi expression vectors may comprise a replication origin, an appropriate promoter and enhancer as well as any necessary ribosome binding sites, polyadenylation sites, splice donor sites and splice acceptor sites, transcription termination sequences and non-transcribed 5'-flanking sequences.

Examples of appropriate host cells are: fungi cells of the genus *Aspergillus, Rhizopus, Trichoderma, Neurospora, Mucor, Penicillium* etc. such as yeasts of the genera *Kluyveromyces, Saccharomyces, Schizosaccharomyces, Trichosporon, Schwanniomyces, Hansenula, Pichia* and the like. Appropriate host systems are, for example, fungi such as *Aspergilli*, e.g., *Aspergillus niger* (ATCC 9142) or *Aspergillus ficuum* (NRLL 3135), or *Trichoderma* (e.g., *Trichoderma reesei* QM6a) and yeasts such as *Saccharomyces*, e.g., *Saccharomyces cerevisiae*, or *Pichia* such as, e.g., *Pichia pastoris*, or *Hansenula*, e.g., *H. polymorpha* (DSMZ 70277). Such microorganisms may be obtained from established depositary institutions, e.g., the American Type Culture Collection (ATCC), the Centraalbureau voor Schimmelcultures (CBS) or the Deutsche Sammlung für Mikroorganismen and Zellkulturen GmbH (DSMZ) or any other depositary institution.

The expression cassette may include, in the 5'-3' transcription direction, a transcription start region and translation start region of the polynucleotide according to the invention and a transcription region and termination region that are functional in vivo or in vitro. The termination region may be native regarding the transcription initiation region or may be native or of other origin regarding the polynucleotide. The regulator sequences may be located upstream (5' non-coding sequences), inwardly (introns) or downstream (3' non-coding sequences) of a coding sequence and may influence the transcription, the RNA processing or the stability and/or the translation of the associated coding sequence. Regulator sequences may comprise without limitation enhancers, promoters, repressor binding sites, translation leader sequences, introns or polyadenylation signal sequences. They may comprise natural and synthetic sequences as well as sequences which are a combination of synthetic and natural sequences.

The vector used according to the invention may also comprise appropriate sequences for the amplification of the expression.

Examples of promoters which may be used according to the invention are promoters of which is known that they control the expression in the eukaryotic cells. Any promoter with the ability to express in filamentous fungi may be used. Examples are a promoter that is strongly induced by starch or cellulose, e.g., a promoter for glucoamylase or α-amylase from the genus *Aspergillus* or for cellulase (cellobiohydrolase) from the genus *Trichoderma*, a promoter for enzymes in the glycolytic metabolic pathway such as phosphoglycerate kinase (PGK) and glycerol aldehyde-3-phosphate dehydrogenase (GPD) etc. The cellobiohydrolase-1 promoter, the cellobiohydrolase-II promoter, the amylase promoter, the glucoamylase promoter, the xylanase promoter or the enolase promoter is preferred.

In addition to the use of a special promoter, other types of elements may influence the expression of transgenes. It was particularly demonstrated that introns have the potential to amplify transgene expression.

The expression cassette may comprise further elements, for example elements which may be regulated by endogenous or exogenous elements such as zinc finger proteins, including naturally occurring zinc finger proteins or chimeric zinc finger proteins.

The expression cassette used according to the invention may also comprise enhancer elements or upstream promoter elements.

Vectors for the use according to the invention may be constructed in such a way that they comprise an enhancer element. Thus, the constructs according to the invention comprise the gene of interest together with a 3' DNA sequence, which acts as a signal to terminate the transcription and to allow for the polyadenylation of the thus obtained mRNA. Any signal sequence which makes the secretion from the selected host organism possible may be used. A preferred signal sequence is the phospholipase signal sequence from *Aspergillus fumigatus* or signal sequences derived therefrom for the secretion from filamentous fungi.

A special leader sequence may also be used, since the DNA sequence between the transcription start site and the start of the coding sequence, i.e., the non-translated leader sequence, may influence the gene expression. Preferred leader sequences comprise sequences which control the optimal expression of the adhered gene, i.e., they comprise a preferred consensus leader sequence, which increases or maintains the mRNA stability and prevents an inappropriate translation initiation. The selection of such sequences is well known to a person skilled in the art.

In order to improve the possibility to identify the transformants, a selectable or screenable marker gene may be included in the expression cassette. Such marker genes are well known to a person skilled in the art.

The expression cassette or a vector construct which comprises the expression cassette is introduced into a host cell. A variety of techniques is available and well known to a person skilled in the art of introducing constructs into a host cell. The transformation of microbial cells may be carried out by means of polyethylene glycol, calcium chloride, viral infection, DEAE dextran, phage infections, electroporation and other methods known in the state of the art. The transformation of fungi may be carried out according to Penttila et al., Gene 61:155-164, 1987. The introduction of a recombinant vector into yeasts may be carried out according to methods known per se, including electroporation, use of spheroplasts, lithium acetate and the like.

As soon as the expression cassette or the DNA sequence according to the invention is obtained, it may be introduced into vectors according to processes known per se in order to over-express the encoded polypeptide in appropriate host systems. However, DNA sequences as such may also be used to transform appropriate host systems of the invention in order to obtain an overexpression of the encoded polypeptide.

As soon as a DNA sequence according to the invention is expressed in an appropriate host cell in an appropriate medium, the encoded phospholipase may be concentrated and/or isolated according to processes known per se either from the medium, if the phospholipase is secreted into the medium, or from the host organism, if the phospholipase is intracellularly present, e.g., in the periplasmic space. Known processes for the separation of the insoluble parts of the culture medium and the biomass followed by processes for concentrating the phospholipase may be used to produce concentrated phospholipase solutions or to prepare the drying of the phospholipase. For example, filtration processes or centrifugation processes may be used for the removal of the insoluble components followed by ultrafiltration processes for concentration, or cross flow filtration processes are used. Drying may be carried out by means of freeze or spray drying, granulation processes, extrusion or other processes. Known processes of protein purification may be used to isolate the phospholipases according to the invention. For example, various chromatographic or gel chromatographic processes may be used individually or in combination. Depending on the host cell used in a recombinant production process, the enzyme according to the invention may or may not be covalently modified by means of glycosylation. In eukaryotic cells the glycosylation of the secreted proteins provides a basis for the modulation of the protein folding, the conformation stability, the thermal stability and the resistance against proteolysis. As regards a specific use of the phospholipase, a glycosylated variant of the enzyme may be preferred to a non-glycosylated variant.

The invention also relates to isolated or basically purified nucleic acid compositions and protein compositions. An isolated and purified polynucleotide/polypeptide or segment thereof refers to a polynucleotide or polypeptide or segment thereof which is isolated from its native environment and is present in a purified form for further use. An isolated polynucleic acid segment or polypeptide may be present in a purified form or may be present in a non-native environment such as in a transgenic host cell. For example, an isolated or purified polynucleotide segment or protein or a biologically active part thereof is basically free of further cellular material or culture medium if produced according to recombinant techniques or is basically free of chemical precursors or other chemical compounds. An isolated polynucleotide is preferably free of sequences (preferably protein-encoding sequences) which naturally flank the nucleic acid (i.e., sequences which are localized at the 5' end and 3' end of the nucleic acid) in the genomic DNA of the organism from which the nucleic acid is derived. For example, according to different embodiments, the isolated nucleic acid molecule may comprise less than approximately 5 kb, 4 kb, 3 kb, 2 kb, 1 kb, 0.5 kb or 0.1 kb of nucleotide sequences which naturally flank the nucleic acid molecule in the genomic DNA of the cell from which the nucleic acid is derived. A protein that is basically free of cellular material comprises compositions of protein and polypeptide with less than approximately 70%, 50%, 30%, 20%, 10%, 5% (in relation to the dry weight) of contaminating protein. If the protein according to the invention or a biologically active fragment thereof is recombinantly produced, the culture medium preferably comprises less than approximately 70%, 50%, 30%, 20%, 10% or 5% (in relation to the dry weight) of the chemical precursors or non-protein-like chemical substances.

The invention also relates to phospholipase compositions which comprise the polypeptide according to the invention. Phospholipase compositions are generally liquid or dry. Liquid compositions preferably comprise the phospholipase enzyme in a purified or enriched form. However, auxiliary agents such as a stabilizer and/or glycerol, sorbitol or monopropylene glycol, additives such as salts, sugar, preservatives, agents to adjust the pH value and proteins may be added. Typical liquid compositions are aqueous or oily suspensions.

Dry compositions may be freeze-dried, spray-dried, granulated or extruded compositions, which may only comprise the enzyme. Dry compositions may be granulates which may easily be mixed with, for example, food or, feed components, or which preferably form a component of a premix. Preferably, the particle size of the enzyme granulate is compatible with that of the other component of the mixture. This allows for safe and purposeful agents to incorporate enzymes in processed food, premixes or animal feed, for example.

Dry compositions may also comprise other additives such as salts, particularly phosphate salts and their anhydrous forms, and stabilizers such as poly(vinyl pyrrolidone) etc. to regulate certain conditions such as the pH value in the application.

A food additive according to this embodiment of the present invention may be combined with other food components in a similar way, whereby processed food products are produced. Such other food components comprise one or more enzyme supplements, vitamins, minerals or trace elements. The thus obtained combined dietary supplement may then be mixed with other food components such as grain and plant proteins in an appropriate amount to obtain processed food. The processing of these components to processed food may be carried out by means of processing devices known per se.

In a preferred embodiment the phospholipase compositions according to the invention additionally comprise an effective amount of one or more enzyme(s) for food or animal feed or for the application in pre-stages for the production of food or animal feed or for the application in textile industry, preferably selected from alpha-galactosidases, beta-galactosidases, laccases, other phospholipases, phosphatases, endoglucanases, particularly endo-beta-1,4-glucanases, endo-beta-1,3(4)-glucanases, endo-1,2-beta-glucanases and endo-1,3-alpha-glucanases, cellulases, xylosidases, galactanases, particularly arabinogalactan-endo-1,4-beta-galactosidases and arabinogalactan-endo-1,3-beta-galactosidases, pectin-degrading enzymes, particularly pectinases, pectinesterases, pectinlyases, polygalacturonases, arabananases, rhamnogalacturonases, rhamnogalacturonanacetylesterases, rhamnogalacturonan-alpha-rhamnosidases, pectate lyases and alpha-galacturonidases, mannanases, beta-mannosidases, mannan acetylesterases, xylan acetylesterases, proteases, xylanases, arabinoxylanases, lipolytic enzymes such as lipases, digalactosid-diglycerol esterases and cutinases, and other enzymes such as laccases and transglutaminases.

The phospholipases according to the invention may be used for a variety of applications. Examples are applications in baking and in animal feeding as well as in the production of fuels from renewable energy sources such as rapeseed, or in the processing of textile raw materials.

A preferred application is the use of the polypeptides having phospholipase activity according to the invention in processes for the degumming of vegetable oil. The edible oil to be degummed is, for example, treated with a polypeptide according to the invention, whereby the majority of the phospholipids is hydrolyzed, and subsequently the aqueous phase containing the hydrolyzed phospholipids is separated from the oil. Such a process is particularly suitable for the purification of edible oils containing phospholipids, for example, vegetable oils such as soy bean oil, rapeseed oil and sunflower oil.

Prior to the phospholipase treatment, the oil is preferably pre-treated to remove gummy substances, for example, by humid refining. Typically, the oil comprises 50 to 850 ppm phosphorus as phospholipid at the beginning of the treatment with the phospholipase according to the invention. After the treatment, the phosphorus content is typically between 2 and 10 ppm.

The phospholipase treatment is generally carried out in such a way that the phospholipase is dispersed in an aqueous solution, preferably in the form of droplets of an average diameter of <10 µm. The amount of water is preferably 0.5 to 5 wt. % (w/w) in relation to the oil. An emulsifier may optionally be added. It may be mechanically stirred to maintain an emulsion. The treatment with phospholipase may be carried out at a pH value in the range of approximately 3.5 to approximately 5.0. The pH value of the process may be in the range of approximately 3.5 to approximately 5, preferably 3.8 to 4.5 and most preferably 4.0 to 4.2 to maximize the performance of the enzyme. The pH value may be adjusted by, e.g., addition of citric acid, a citrate buffer, phosphoric acid or hydrochloric acid. An appropriate temperature is generally 30°-70° C., preferably 45°-65° C. and most preferably 55°-62° C. The reaction time is typically 1 to 12 hours, preferably 2 to 6 hours. An appropriate enzyme dosage is usually 120 to 3,000 units per kg oil, preferably 250 to 2,000 and most preferably 750 to 1,500 units per kg oil.

The phospholipase treatment may be carried out batchwise, for example in a tank under stirring, or may be continuous, for example, in a series of tank reactors under stirring.

The phospholipase treatment is followed by the separation of an aqueous phase and an oily phase. The separation may be carried out by conventional means, for example, centrifugation. The aqueous solution contains phospholipases, and the enzyme may be used again to improve the economy of the process.

The treatment may be carried out by means of processes known per se.

Advantageously, the phospholipase according to the invention may also be used to prepare dough and bakery products, whereby an effective amount of a polypeptide according to the invention is worked into the dough. By adding a polypeptide having phospholipase activity according to the invention, one or several property(ies) of the dough or the bakery product prepared by means of the dough may be improved compared to a dough or bakery product to which no polypeptide having phospholipase activity according to the invention was added.

In the dough preparation by means of the phospholipase according to the invention the phospholipase may be added to the dough itself, to any ingredient of which the dough is prepared, and/or to a mixture of dough ingredients of which the dough is prepared. A polypeptide having phospholipase activity according to the invention may thus be added as such in any step of the dough preparation or may be added in one, two or more step(s). Here an effective amount is to refer to an amount of phospholipase that is sufficient to cause a measurable effect on at least one property of interest of the dough and/or the bakery product.

The expression "improved property" is defined herein as any property of the dough and/or the product that is obtained from the dough, particularly a bakery product, which was improved due to the effect of the phospholipase in relation to the dough or the product to which the phospholipase according to the invention was not added. The improved property may comprise, for example: improved dough strength, improved elasticity of the dough, improved stability of the dough, reduced stickiness of the dough, improved extensibility of the dough, improved machinability of the dough, increased volume of the bakery product, improved crumb structure of the bakery product, improved softness of the bakery product, improved aroma of the bakery product and/or delayed staling of the bakery product. Processes to determine these properties are well known in the state of the art.

Dough is herein defined as a mixture of flour and other ingredients, which is solid enough to be kneaded or rolled. The dough may be fresh, frozen, precooked or pre-baked.

The expression "bakery product" herein refers to any product which is prepared by dough and is either soft or crisp. Examples of bakery products which may be prepared by means of a phospholipase according to the invention are, for example, bread (particularly white bread, wholemeal bread or rye bread), typically in the form of loaves or French bread of the type French baguette, pasta, pita bread, tortillas, tacos, cakes, pancakes, cookies and pastries, cooked bread, double-baked bread and the like.

In the preparation of these bakery products the polypeptide having phospholipase activity according to the invention and/or one or more further enzyme(s) in any formulation that is suitable for the respective use may be added, for example, in a dry form, as a liquid or as a premix. Furthermore, one or more further enzyme(s) may be added to the dough. These further enzymes may be of any origin and may be derived from mammals and plants, for example. Preferably, they are of a microbial origin and are particularly preferably derived from bacteria or fungi.

According to a preferred embodiment, the further enzymes may be amylases such as α-amylase (suitable for producing sugars that are fermentable by yeasts and for delaying staling) or β-amylase, cylcodextrin glucanotransferase, peptidase, particularly an exopeptidase (suitable for increasing the aroma), transglutaminase, lipase (suitable for modification of the lipids present in the dough or in parts of the dough to make the dough softer), phospholipase (useful for modification of the lipids that are present in the dough or in parts of the dough to make the dough softer and to improve the gas retention in the dough), cellulase, hemicellulase, particularly a pentosanase such as xylanase (useful for the partial hydrolysis of pentosanes which improve the extensibility of the dough), proteases (useful for gluten softening, particularly if durum flour is used), protein disulphid isomerase (for example, a protein disulphid isomerase disclosed in WO 95/00636), glycosyl transferase, peroxidase (useful for improving the consistency of the dough), laccase or oxidase, for example, an aldose oxidase, glucose oxidase, pyranose oxidase, lipoxygenase or L-amino acid oxidase (useful for improving the consistency of the dough).

This/These optionally further added enzyme/enzymes may be optionally added separately or together with the polypeptide having phospholipase activity according to the invention as components of baking agents or dough additives. The invention also relates to the preparation of such doughs as well as to the preparation of corresponding bakery products made of these doughs.

The invention also relates to a premix, for example, in the form of a flour composition, for the preparation of dough and/or bakery products made of dough, whereby this premix comprises polypeptides having phospholipase activity according to the invention.

The polypeptides having phospholipase activity according to the invention may also be used as additives to animal feed. Adding phospholipases to feed improves the efficiency of feed conversion of animals. Thus the growth of animals which are nourished with such feed is improved. A phospholipase according to the invention may hereby be added as such or as feed concentrate. Furthermore, the phospholipase may also be added to the animal feed via transgenic plants, wherein the phospholipase was synthesized by heterologous gene expression. Processes for the production of such transgenic plants are disclosed in EP0449376:

The polypeptides having phospholipase activity according to the invention may also be used in the process of scouring in the processing of textile raw materials such as cotton fibres to facilitate the further treatment of the fibres. The improvements obtained by scouring influence the behavior during staining as well as the further mechanic and enzymatic processing of the fibre and the fabric made thereof.

The gene for the phospholipase which was isolated from the microorganism *Aspergillus fumigatus* was deposited in the plasmid pPL3949-Topo2.5 under accession number DSM 22741 at the Deutsche Sammlung von Mikroorganismen and Zellkulturen GmbH (DSMZ), Inhoffenstraße 7B, D-38124 Braunschweig on Jul. 2, 2009 in accordance with the provisions of the Budapest Treaty.

The invention is further described on the basis of the enclosed figures. It is shown in:

FIG. 1: IEF gel of purified phospholipase from *Aspergillus fumigatus*.

Track 1: marker protein from the Isoelectric Focusing Calibration Kit, pH 2.5-6.5, Track 2-3: The phospholipase band at pI approx. 4.1 is identified by an arrow.

Figure 2:
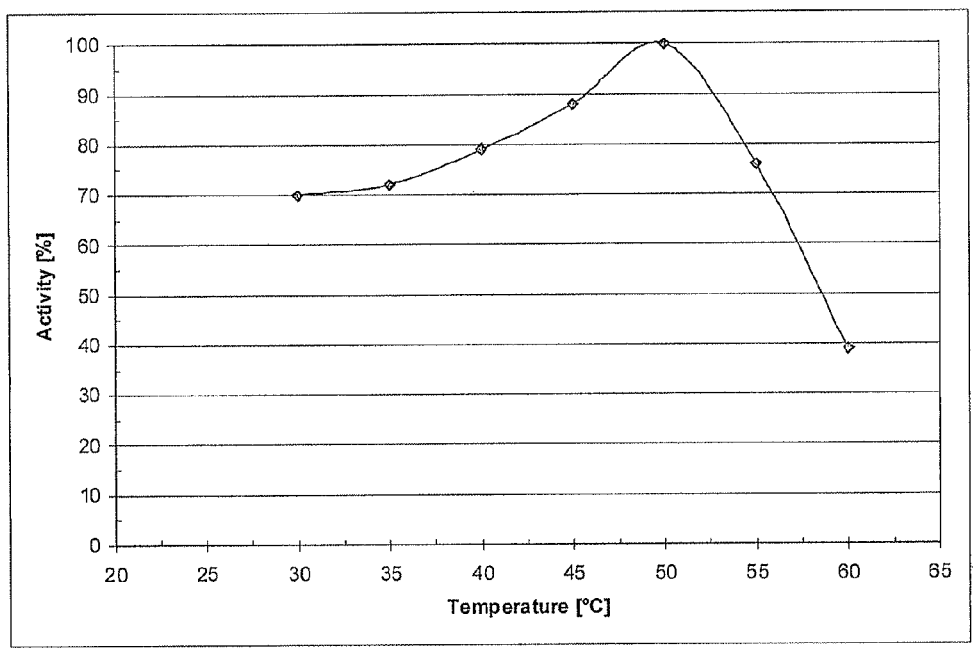

FIG. 2: T optimum curve for the recombinant phospholipase expressed in *Trichoderma reesei* RH32664.

Figure 3:
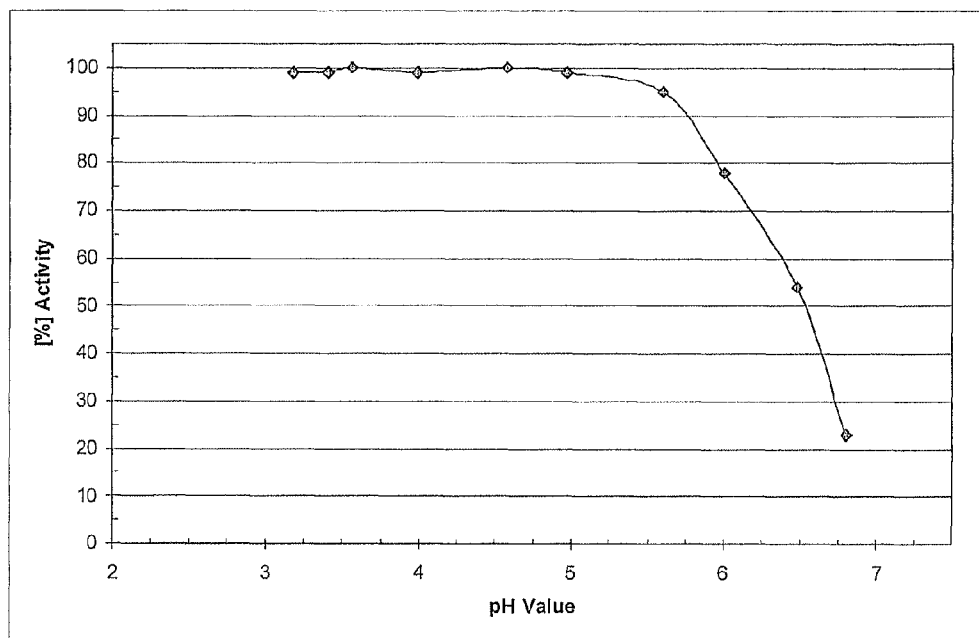

FIG. 3: pH optima curve for the recombinant phospholipase expressed in *Trichoderma reesei* RH32664.

FIG. 4A and FIG. 4B: Nucleotide sequence and amino acid sequence derived therefrom of the chromosomal phospholipase gene from *Aspergillus fumigatus* RH3949. The introns are printed in italics and the amino acid sequence in bold face type (nucleotide sequence disclosed as SEQ ID NO: 1, amino acid sequence disclosed as SEQ ID NO: 2).

FIG. 5: The nucleotide sequence of the chromosomal phospholipase gene from *Aspergillus fumigatus* RH3949 (SEQ ID NO: 1).

FIG. 6: The amino acid sequence of the phospholipase gene from *Aspergillus fumigatus* RH3949 (SEQ ID NO: 2).

FIG. 7: Restriction map of the vector pPL3949-Topo2.5

Figure 8:
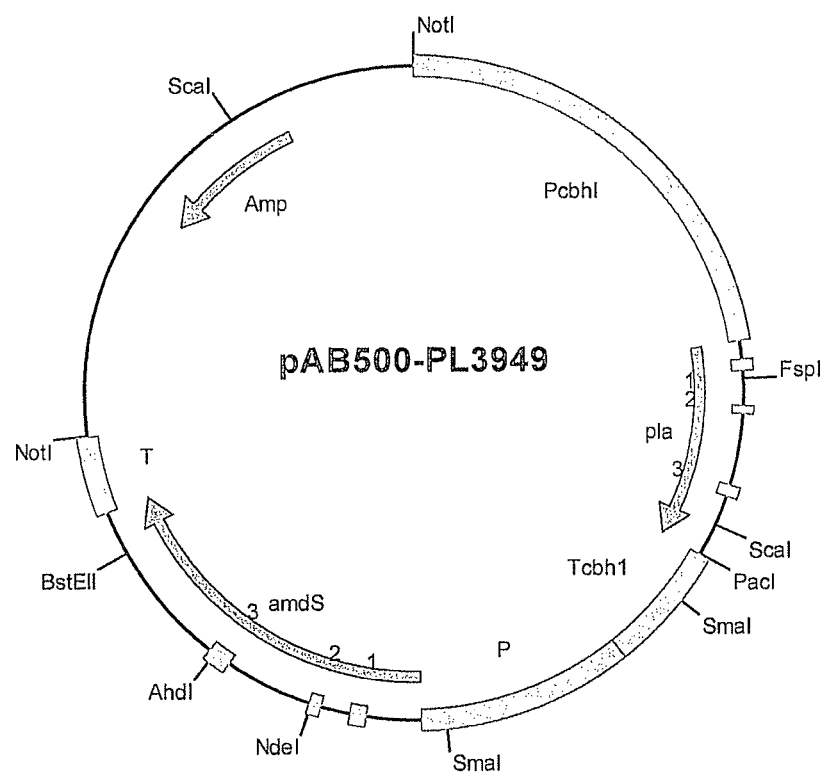

FIG. 8: Restriction map of the expression vector pAB500-PL3949

REFERENCE EXAMPLE 1

Determination of the Phospholipase Activity 1 phospholipase unit (PLU) corresponds to the amount of enzyme which releases 1 μmol fatty acid per minute from the phosphatidyl choline under standard conditions.

Reagents:

Substrate Emulsion:

1 g Epikuron 200 (purified phosphatidyl choline derived from soy of the company Lucas Meyer, now available at Cargill), 100 ml deionized water and 5 ml 0.32 M $CaCl_2$ solution are homogenized by means of an Ultra Turrax for 2 min at 24,000 rpm. The substrate emulsion is stable at 4°-8° C. for 3-4 d.

Other Solutions:

0.32 $MgCl_2$ solution, fresh 3.3 mM citric acid-monohydrate solution, 10 mM KOH solution, 1% Triton X100 (company Fluka) solution in demineralized water Enzyme Solution:

The enzyme preparations are dissolved in deionized water. The enzyme concentration in the batch may not exceed 2.5 U $g^{-1}$.

Procedure:
Main values
10 ml substrate emulsion
10 ml 1% Triton X100 solution
5 ml 3.3 mM citric acid-monohydrate solution
were pipetted in a 25 ml wide-necked Erlenmeyer flask and tempered at 40° C. for 10 min. The pH value adjusts to approximately 3.3-3.5.

After adding 0.1 ml of enzyme solution, the analysis batch was incubated for 10 min at 40° C. When the incubation time is over, the solution is titrated with 10 mM KOH to pH 10.0, whereby the first 5 ml of KOH are added rapidly (duration: about 1 min). The consumption of KOH is registered.

Blank Values

The enzyme parent solution is heated for 15 min at 95° C. and is thus deactivated. After cooling down to room temperature, the further treatment is the same as for the main values.

An incubation of the blank values is not necessary.

Evaluation:

$$PLU/g = \frac{\Delta V_{KOH} * c_{KOH} * 1000}{\Delta t * c_s * v}$$

$V_{KOH}$ (ml) difference in consumption between the blank value and the main value
$c_{KOH}$ (mol l$^{-1}$) concentration of the KOH solution
$\Delta t$ (min) incubation time
$c_s$ (g ml$^{-1}$) concentration of the sample
v (ml) volume used

REFERENCE EXAMPLE 2

Rapid Test for the Detection of Phospholipase at pH 3.5

Reagents:
Substrate Emulsion:
1 g Epikuron-200 is mixed with 100 mg Milli Q Water and 5 ml 0.32 M calcium chloride solution and is homogenized by means of the Ultra-Turrax (for about 1-2 min at about 24000 rpm).

For the analysis batch 10 ml of this substrate emulsion are mixed with 10 ml of 1% Triton X-100 solution and 5 ml of 3.3 mM citric acid solution-monohydrate solution.

Free Fatty Acids, Semi-Micro Test (Boehringer)

(The semi-micro test contains the reagents for the reaction mixture A, reaction mixture B and the N-ethylmaleimide).

Procedure:

At first 5 μl diluted enzyme solution are provided in the microtiter plate and mixed with 0.1 ml substrate emulsion.

The substrate/enzyme batches are incubated in a water bath for 10 min at 40° C.

Subsequently, 5 μl of the batch are pipetted into a second microtiter plate to 100 μl of the reaction mixture A and are incubated for 5 min at 40° C.

After the incubation time is over 5 μl of a mixture of reaction mixture B and N-ethylmaleimide solution at a ratio of 1:1 are added and again incubated for 5 min at 40° C.

Phospholipase activity is present if the reaction batch gets a red color.

REFERENCE EXAMPLE 3

Determination of the Content of Free Fatty Acids

Reagents:
Ethanol (96% solution), toluol
Ethanol and toluol are mixed in the ratio 1:1 (v/v).
0.1 N ethanolic KOH
1% phenolphthalein solution in ethanol Procedure:
Approximately 3 g water-free oil are weighed out into an Erlenmeyer flask to four decimal places exactly, dissolved in 20 ml ethanol-toluol mixture, mixed with 2 to 3 drops of phenolphthalein and titrated with 0.1 N KOH solution until it has a lasting red color.

Evaluation:
The acid number is an indicator for the content of free fatty acids. The acid number refers to the amount of potassium hydroxide in g necessary for the neutralisation of the free fatty acids contained in 1 kg oil. The acid number (AN) is calculated according to the following equation:

$$AN = \frac{a * N * 56.1}{E}$$

a amount of KOH solution in ml used
N normality of KOH
E amount of fat in g weighed out
56.1 molar mass of KOH in g/mol The acid number may be used to calculate the content of free fatty acids (FFA) in percent:

$$FFA (\%) = AN * \frac{282 * 100}{56.1 * 1000}$$

282 molar mass of the oleic acid

REFERENCE EXAMPLE 4

Detection of Lipase

The qualitative detection of lipase on olive oil-agar is analogously carried out according to the method of Kouker and Jaeger (Applied Environ. Microbiol., 59: 211-213 (1987)).

For the detection of lipase activity agar plates made of tributyrin agar (Fluka 91015) which were produced with 1% olive oil are used. The pH value adjusts to 5.5.

The detection of lipase activity is photometrically carried out with emulsified p-nitrophenylpalmitate (Sigma N2752) as a substrate in 0.5 M citrate/phosphate buffer, pH 5.1 according to Winkler and Stuckmann (1979) (J. Bac., 138: 663-670 (1979)).

EXAMPLE 1

Extraction of Phospholipase from *Aspergillus fumigatus* Strain RH3949

*Aspergillus fumigatus* was grown in 200 ml shaking flasks filled with 50 ml medium at 28° C., 200 rpm, over 5 d. The medium consisted of 0.5% Epicuron 200 (Lucas Meyer), 0.5% corn steep powder, 0.2% NH$_4$NO$_3$, 100 mM KH$_2$PO$_4$ and 0.1% Triton X100. The pH value was adjusted to pH 6 before sterilisation. The medium was inoculated with a spore suspension. After 5 days the culture supernatant was separated from the mycelium by means of filtration and the phospholipase activity in the liquid was measured.

EXAMPLE 2

Purification of the Phospholipase from *Aspergillus fumigatus* Strain RH3949

Step 1: Anion Exchanger, Macro Prep Q

In order to purify the phospholipase at first a separation of proteins was carried out at the anion exchanger Macro Prep Q.

To this end the concentrated culture supernatant from the cultures according to example 1 was diluted with completely desalinated water until the protein solution had the same conductivity as buffer A. Subsequently, the protein sample was adjusted to pH 7 with 1 M NaOH and loaded onto the column equilibrated with buffer A. After washing the column with buffer A the phospholipase was eluted with a linearly increasing NaCl gradient of 0-1 M. The fractions having phospholipase activity were combined and further purified.

Buffer A: 5 mM $CaCl_2$+20 mM Tris-HCl, pH 7.0
Buffer B: 5 mM $CaCl_2$+20 mM Tris-HCl, pH 7.0+1 M NaCl Step 2: HIC, Phenyl Sepharose 6 Fast Flow Low Substitution The protein sample having phospholipase activity according to step 1 was mixed with 3.4 M ammonium sulphate solution at a ratio of 1:1 and adjusted to pH 7.0 with 1 M NaOH solution. After applying the sample to the phenyl-sepharose column, which was also equilibrated with buffer A, the phospholipase was eluted with a decreasing ammonium sulphate gradient.

Buffer A: 5 mM $CaCl_2$+20 mM Tris-HCl, pH 7.0+1.7 M ammonium sulphate
Buffer B: 5 mM $CaCl_2$+20 mM Tris-HCl, pH 7.0

Step 3: Gel Filtration, Superose 12 HR 10/30

As a final purification step the proteins were separated at a gel filtration column. To this end the phospholipase sample according to step 2 was dialyzed against completely desalted water in a dialyse tube (Naturin protein farce) for 1.5 h and subsequently lyophilised. The lyophilisate was absorbed in 500 μl completely desalinated water. 250 μl were applied to the column in two steps, respectively, and eluted with buffer A.

Buffer A: 5 mM $CaCl_2$+20 mM Tris-HCl, pH 7.0

The purified phospholipase was applied to an IEF gel. The result is displayed in FIG. 1.

The bands were cut out for identification and examined for phospholipase activity according to the described method of analysis.

EXAMPLE 3

N-Terminal Protein Sequencing

After the final purification step via the superose the purified protein was separated on a native gel. The protein bands having phospholipase activity were cut out and again applied to an SDS gel in order to determine the molecular weight. For the determination of N-terminal amino acids the protein bands were transferred from the native gel to a PVDF membrane (Fluotrans Transfer Membrane, Pall) and the N-terminal amino acid sequences were determined in an amino acid sequencer (Applied Biosystems Model 470A) according to the Coomassie staining process. They are:

$^1$DVSAS VLQKL SLFAQ Y$^{16}$ (SEQ ID NO: 3)

Comparing the sequences shows that the N-terminal amino acid sequence of the phospholipase gene has a high sequence similarity with the gene of the extracellular lipase from the *Aspergillus fumigatus* strain Af293 (GenBank EAL86100).

EXAMPLE 4

Cloning of the Chromosomal Phospholipase Gene from the *Aspergillus fumigatus* Strain RH3949 by Means of Polymerase Chain Reaction (PCR)

Different oligoprimers for the amplification of the phospholipase DNA were derived from the data of the chromosomal DNA sequence of the *Aspergillus fumigatus* lipase. The chromosomal DNA preparation was carried out according to modified instructions of Hynes, M. J et al., (1983) Mol. Cell. Biol. 3, 1430-1439. The amplification of the phospholipase gene was carried out by means of the PCR method. The PCR products were cloned in pCR2.1-TOPO plasmid and sequenced. Hereby it is shown that the primer pair N2-3948 and 3949-ApaI leads to the gene having the phospholipase DNA according to the invention.

```
N2-3948
                                        (SEQ ID NO. 4)
5'-AGAGTCTGCC TATATTCTCT CTGAAAGG-3'

3949-ApaI
                                        (SEQ ID NO: 5)
5'-TATGACAATTTCCGTGATTACTG-3'
```

The reaction batch of 100 μl comprised: 10 μl 10× buffer (200 mM Tris/HCl, pH 8.4, 500 mM KCl), 3 μl 50 mM $MgCl_2$, 2 μl 10 mM dNTP, 50 pMol oligoprimer (N2-3948 and 3949-ApaI) each, approx. 10 ng chromosomal DNA, 5 U Taq DNA polymerase (Invitrogen). The batch was treated for denaturation at 95° C./5 min, 45 cycles (95° C./1 min, 45° C./1 min, 72° C./1 min) and the subsequent extension was carried out at 72° C./10 min.

The PCR products were purified on a Qiaquick column and cloned in pCR2.1-TOPO plasmid. After sequencing one transformant comprised the phospholipase DNA sequence according to the invention (FIG. 5, SEQ ID NO: 1) and was referred to as pPL3949-Topo2.5 (FIG. 7).

The open reading frame which codes for the phospholipase comprises 1052 nucleotides containing 299 amino acids. The Phospholipase gene comprises 3 introns.

The derived N-terminal amino acid sequence corresponds to the peptide sequences determined by means of protein sequencing (Example 3, SEQ ID NO: 3).

The derived molecular weight of approx. 28.6 kDa corresponds to the approx. 29 kDa which were determined by means of SDS-PAGE (Example 8).

The determination of the signal sequence was carried out with the help of a computer program (PSORT) by Nakai and Kanehisa (1992, Genomics 14, 897-911). According to this program the phospholipase gene has a signal sequence of 21 amino acids and a propeptide of 8 amino acids.

EXAMPLE 5

Construction of the Expression Vector pAB500-PL3949

In the expression vector pAB500-PL3949 the phospholipase gene is under control of the *T. reesei* cbhI promoter and cbhI terminator.

For the construction of the plasmid pAB500-PL3949 the gene coding for phospholipase was amplified from the plasmid pPL3949.Topo2.5 by means of PCR. The PCR product was hydrolysed with the enzymes AvrII/PacI and subsequently inserted in the SpeI and PacI cleavage sites after the *T. reesei* cbh1 promoter in the plasmid pAB500. The plasmid obtained is referred to as pAB500-PL3949.

The construction of the plasmid pAB500 was carried out according to the following steps:

By introducing further cleavage sites (SpeI and PacI in the SacII site between the cbhI promoter and the cbhI terminator) the plasmid pAB487 was produced from the plasmid pALK487 (WO94/28117). The SpeI-PacI cleavage sites are used for the direct cloning of the phospholipase gene.

The amdS gene including its promoter and its terminator was amplified from the plasmid p3SR2 (GenBank 16371) by means of PCR. The PCR product was cut with AscI and NruI and inserted in the AscI/StuI cleavage site of pAB487, whereby the plasmid pAB500 was obtained.

EXAMPLE 6

Transformation of *T. reesei*

The techniques used for the transformation and treatment of *T. reesei* were those according to Penttila et al. (1987, Gene 61: 155-164).

*T. reesei* RH32439 was transformed with the linearized expression cassette isolated from the plasmid pAB500-PL3949.

The transformants were selected and purified by means of single spore isolation. Of all transformants, those having the highest secretion capacity were chosen and further used in Example 7 for the production of enzyme material.

EXAMPLE 7

Production of Enzyme Solutions by Means of Fermentation in Shaking Flasks

Transformants which carry the expression cassette of Example 6 were cultivated on a cellulase-induced medium in shaking flasks. The culture filtrates obtained after 6 days of growing were used for the characterization of the enzyme (Example 8) and for the analysis of the oil degumming process (Example 9).

EXAMPLE 8

Characterization of the Recombinant Phospholipases

The determination of the molecular weight by means of SDS polyacrylamide gel electrophoresis (SOS-PAGE) resulted in a molecular weight of approx. 29 kDa for the phospholipase according to the invention.

The N-terminal sequencing of the recombinant phospholipase was carried out by the company Chromatec (Germany).

The amino acid sequence obtained by means of sequencing corresponds to the N-terminal sequence of the phospholipase (Example 3).

The identification of the recombinant protein by means of MALDI-MS was carried out by the company Protagen (Germany). The result confirms that the protein sequence of the phospholipase according to the invention is correct.

The temperature dependency of the enzyme activity was determined at different temperatures by means of the determination method as described above. The temperature optimum of the phospholipase is 50° C. (cf. FIG. 2).

The optimal pH value of the enzyme activity was determined at different pH values by means of the determination method as described above. To this end the pH value in the reaction batch was adjusted with the help of citric acid.

The enzyme is active in a broad pH range of pH 3 to 5 (cf. FIG. 3).

The lipase activity was determined by means of the determination method described above. The *A. fumigatus* phospholipase according to the invention has a very low lipase activity. According to the calculations the ratio of phospholipase activity to lipase activity was 7480:1 (with an experimental variation limit of ±10%).

EXAMPLE 9

Degumming of Oil by Means of an Enzyme from Culture Supernatants of Recombinant *Trichoderma reesei* Strains Having the Gene from *A. fumigatus* RH3949

200 g edible oil (soybean oil 1 with a phosphorus content of 163.6 ppm; rapeseed oil with a phosphorus content of 161.6 ppm; soybean oil 2 with a phosphorus content of 592.8 ppm and soybean oil 3 with a phosphorus content of 81.1 ppm) were mixed with 0.42 ml of a 46% citric acid solution and water in a 400 ml beaker glass. Thereby the total water content should not exceed 2%. The pH value of the reaction mixture was adjusted to pH 4.0 by adding a 7% NaOH solution (0.6 ml). After adding the enzyme solution according to the invention (50 U) the reaction batch was mixed with the help of an Ultra Turrax for 2 min at 24000 rpm. Subsequently, the mixture was filled into a three-necked round-bottomed flask and incubated at 55° C. or 60° C. while stirring gently (200 rpm).

A sample of 20 ml was taken each 120 min after addition of the enzyme solution. The samples were centrifuged for 5 min at 4300×g and the phospholipide content, shown in ppm phosphorus, was photometrically determined as phosphorus molybdate complex at 830 nm in the oil after ashing at 850° C. by adding magnesium oxide.

The recombinant *Trichoderma reesei* strain which comprises the plasmid pAB500-PL3949 according to the invention is referred to as RH32664.

The results obtained in the process of degumming edible oil at 55° C. or 60° C. by means of a phospholipase derived from a recombinant strain of *Aspergillus fumigatus* RH3949 are shown in Table 2.

The results show a clear degumming effect in the degumming process using the enzyme according to the invention compared to the water degumming process using citric acid. After only 4 hours the content of the remaining phosphorus is less than 10 ppm.

TABLE 2

Degumming of soybean oil and rapeseed oil by means of phospholipase enzymes according to the invention (250 U per kg of edible oil) from culture supernatants of a recombinant *Trichoderma reesei* strain having a water content of 2% at pH 4.0

| name of sample | time (min) | phosphorus content (ppm) temp (° C.) | | |
|---|---|---|---|---|
| | | 55 | 60 | |
| citric acid | 240 | 109.7 | 15.5 | 14.9 |
| | 360 | 117.7 | 13.4 | 15.3 |
| RH32664 (phospholipase) | 240 | 8.4 | 4.1 | 4.6 |
| | 360 | 7.8 | 2.4 | 2.0 |
| soybean oil 1 | untreated | 163.3 | | |
| rapeseed oil | untreated | | 161.6 | |
| soybean oil 2 | untreated | | | 592.8 |

EXAMPLE 10

Content of Free Fatty Acids in the Oil Degumming Process

The determination of the content of free fatty acids in the oil degumming process was carried out as described in reference example 3. The edible oil was mixed with phospholipase as described in Example 9 and incubated for 6 hours at 57° C. The enzymatic hydrolysis of phospholipids was caused by phospholipases which cleave the fatty acid. For reasons of comparison the same analysis was carried out with pure edible oils as blank value.

In contrast to the blank value (BV) the content of free fatty acid (FFA) in the samples rises only slightly and the difference ($\Delta_{FFA}$) is 0.18% after treating the edible oil with phospholipase at a temperature of 57° C. (Table 3).

TABLE 3

Content of free fatty acids after treating the oil with phospholipase

| name of sample | time (min) | phosphorus content (ppm) | FFA (%) | $\Delta_{FFA}$ (%) |
|---|---|---|---|---|
| citric acid | 240 | 37.2 | | |
| | 360 | 42.4 | 0.09 | |
| RH32664 (phospholipase) | 240 | 2.0 | | |
| | 360 | 3.0 | 0.27 | 0.18 |
| soybean oil 3, untreated | | 81.1 | | |

The invention claimed is:

1. An isolated, synthetic, non-natural polypeptide with phospholipase activity essentially without lipase activity selected from the group consisting of:
   a) a polypeptide having the sequence according to SEQ ID NO: 2,
   b) a polypeptide having a sequence that has at least 90% identity with SEQ ID NO: 2, and
   c) a polypeptide which is coded for by a nucleic acid sequence which hybridizes under stringent conditions with
      (i) a DNA sequence comprising a nucleotide sequence according to SEQ ID NO: 1,
      (ii) a DNA sequence comprising the coding sequence according to SEQ ID NO: 1,
      (iii) a DNA sequence that codes for a protein sequence according to SEQ ID NO: 2, or
      (iv) a complementary strand of (i), (ii) or (iii), wherein said DNA sequences hybridize at 65° C., 18 h in dextran sulphate solution, subsequent washing of the filter for 30 min, respectively, at first with 6× saline-sodium citrate (SSC), twice 2×SSC, twice 2×SSC, 0.1% SDS, and with 0.2×SSC at 65° C.

2. The isolated, synthetic, non-natural polypeptide with phospholipase activity essentially without lipase activity of claim 1, characterized in that it has a molecular weight in the range of 28 to 30 kDa, may hydrolyze at least one of the two fatty acids of lecithin, has a high temperature resistance, and may be derived from an organism of the genus *Aspergillus*.

3. The polypeptide according to claim 2 characterized in that it may be derived from *Aspergillus fumigatus*.

4. The polypeptide according to claim 3 characterized in that it is immunologically reactive with an antibody directed against the sequence SEQ ID NO: 2.

5. The polypeptide according to any one of claims 2 to 4 characterized in that it comprises the sequence according to SEQ ID NO: 2.

6. A phospholipase composition characterized in that it comprises a polypeptide according to any one of claims 1 to 5 together with additives and that it optionally further comprises one or more enzyme(s) for food or animal feed.

7. A process for degumming of vegetable oil characterized in that
   a) the vegetable oil to be treated is optionally pre-treated,
   b) an aqueous solution containing a polypeptide according to any one of claims 1 to 5 or a phospholipase composition according to claim 6 is added to the thus optionally pre-treated oil,
   c) the reaction batch according to b) is heated 1 to 12 h to a temperature of between 30° C. and 70° C. and
   d) the aqueous and oily phases are separated.

8. An isolated, synthetic, non-natural polypeptide with phospholipase activity essentially without lipase activity comprising a polypeptide which is encoded for by the coding part of a DNA sequence selected from the group consisting of
   a) DNA sequences that comprise a nucleotide sequence according to SEQ ID NO: 1,
   b) DNA sequences that comprise the coding sequence according to SEQ ID NO: 1,
   c) DNA sequences that code for the protein sequence according to SEQ ID NO: 2,
   d) DNA sequences that are coded for by the plasmid pPL3940-Topo2.5 with the restriction map according to FIG. 7, which is deposited under accession number DSM 22741,
   e) DNA sequences that hybridize under stringent conditions with one of the DNA sequences according to a), b), c) or d), wherein said DNA sequences hybridize at 65° C., 18 h in dextran sulphate solution, subsequent washing of the filter for 30 min, respectively, at first with 6× saline-sodium citrate (SSC), twice 2×SSC, twice 2×SSC, 0.1% SDS, and with 0.2×SSC at 65° C., and
   f) complementary strands to the sequences according to a) to e), wherein the DNA sequence is derived from *Aspergillus*.

9. A polypeptide with phospholipase activity essentially without lipase activity, wherein said polypeptide has an amino acid sequence that is at least 90% identical to SEQ ID NO: 2.

* * * * *